United States Patent
Gong

(10) Patent No.: US 9,321,765 B2
(45) Date of Patent: Apr. 26, 2016

(54) CRYSTALLINE BROMODOMAIN INHIBITORS

(71) Applicant: AbbVie Inc., North Chicago, IL (US)

(72) Inventor: Yuchuan Gong, Waukegan, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 14/317,029

(22) Filed: Jun. 27, 2014

(65) Prior Publication Data

US 2015/0005340 A1 Jan. 1, 2015

Related U.S. Application Data

(60) Provisional application No. 61/840,777, filed on Jun. 28, 2013.

(51) Int. Cl.
*C07D 471/02* (2006.01)
*A61K 31/44* (2006.01)
*C07D 471/04* (2006.01)

(52) U.S. Cl.
CPC .................................. *C07D 471/04* (2013.01)

(58) Field of Classification Search
None
See application file for complete search history.

(56) References Cited

U.S. PATENT DOCUMENTS

| 2005/0137201 A1 | 6/2005 | Aronov et al. |
| 2012/0208814 A1 | 8/2012 | Demont et al. |

FOREIGN PATENT DOCUMENTS

| WO | 2011143651 A1 | 11/2011 |
| WO | 2011143669 A2 | 11/2011 |
| WO | 2013097052 A1 | 7/2013 |

OTHER PUBLICATIONS

Sanchez, R, et al., Biochem. Biophys. Acta 2014, 1839, pp. 676-685.*
Anand P., et al., "BET Bromodomains Mediate Transcriptional Pause Release in Heart Failure," Cell, 2013, vol. 154 (3), pp. 569-582.
Banerjee C., et al., "BET Bromodomain Inhibition as a Novel Strategy for Reactivation of HIV-1," Journal of Leukocyte Biology, 2012, vol. 92 (6), pp. 1147-1154.
Dawson M.A., et al., "Inhibition of BET Recruitment to Chromatin as an Effective Treatment for MLL-fusion Leukaemia," Nature, 2011, vol. 478 (7370), pp. 529-533.
Delmore J.E., et al. "BET Bromodomain Inhibition as a Therapeutic Strategy to Target c-Myc," Cell, 2011, vol. 146 (6), pp. 904-917.
Denis G.V., "Bromodomain Coactivators in Cancer, Obesity, type 2 Diabetes, and Inflammation," Discovery Medicine, 2010, vol. 10 (55), pp. 489-499.
Huang B., et al., "Brd4 Coactivates Transcriptional Activation of NF-kappaB Via Specific Binding to Acetylated ReIA," Molecular and Cellular Biology, 2009, vol. 29 (5), pp. 1375-1387.
International Search Report and Written Opinion for Application No. PCT/US2014/044513, mailed on Sep. 11, 2014, 11 pages.
Jang M.K., et al., "The Bromodomain Protein Brd4 is a Positive Regulatory Component of P-TEFb and Stimulates RNA Polymerase II-dependent Transcription," Molecular Cell, 2005, vol. 19 (4), pp. 523-534.
Leroy G., et al., "The Double Bromodomain Proteins Brd2 and Brd3 Couple Histone Acetylation to Transcription," Molecular Cell, 2008, vol. 30 (1), pp. 51-60.
Liu R., et al., Role of Transcription Factor Acetylation in Diabetic Kidney Disease, Sirt1 and Protein Acetylation in Diabetic Kidney Disease, Diabetes, 2014, 14 pages.
Matzuk M.M., et al., "Small-molecule Inhibition of BRDT for Male Contraception," Cell, 2012, vol. 150 (4), pp. 673-684.
Mertz J.A., et al., "Targeting MYC Dependence in Cancer by Inhibiting BET Bromodomains," Proceedings of the National Academy of Sciences, 2011, vol. 108 (40), pp. 16669-16674.
Nicodeme E., et al., "Suppression of Inflammation by a Synthetic Histone Mimic," Nature, 2010, vol. 468 (7327), pp. 1119-1123.
Spiltoir J.I., et al., "BET Acetyl-Lysine Binding Proteins Control Pathological Cardiac Hypertrophy, "Journal of Molecular and Cellular Cardiology, 2013, vol. 63, pp. 175-179.
Sutton, V.R. et al., "Bcl-2 Prevents Apoptosis Induced by Perforin and Granzyme B, But Not That Mediated by Whole Cytotoxic Lymphocytes," Journal of Immunology, 1997, vol. 158 (12), pp. 5783-5790.
Tang X., et al., "Assessment of Brd4 Inhibition in Idiopathic Pulmonary Fibrosis Lung Fibroblasts and in Vivo Models of Lung Fibrosis," American Journal of Pathology, 2013, vol. 183 (2), pp. 470-479.
Yang Z., et al., "Brd4 Recruits P-TEFb to Chromosomes at Late Mitosis to Promote G1 Gene Expression and Cell Cycle Progression," Molecular and Cellular Biology, 2008, vol. 28 (3), pp. 967-976.
Zhang G., et al., "Down-regulation of NF-kB Transcriptional Activity in HIV-associated Kidney Disease by BRD4 Inhibition," Journal of Biological Chemistry, 2012, vol. 287 (34), pp. 28840-28851.
Zuber J., et al., "RNAi Screen Identifies Brd4 as a Therapeutic Target in Acute Myeloid Leukaemia," Nature, 2011, vol. 478 (7370), pp. 524-528.

* cited by examiner

*Primary Examiner* — Heidi Reese
(74) *Attorney, Agent, or Firm* — Glen J. Gesicki

(57) ABSTRACT

N-[4-(2,4-difluorophenoxy)-3-(6-methyl-7-oxo-6,7-dihydro-1H-pyrrolo[2,3-c]pyridin-4-yl)phenyl]ethanesulfonamide and crystalline forms thereof are suitable pharmaceutical ingredients for pharmaceutical compositions useful in the treatment of disease, for example, cancer.

26 Claims, 6 Drawing Sheets

CRYSTALLINE BROMODOMAIN INHIBITORS

CROSS-REFERENCE PATENT

This patent application claims priority to U.S. Provisional Patent Application No. 61/840,777 filed Jun. 28, 2013. The entire text of this application is incorporated by reference into this patent application.

BACKGROUND OF THE INVENTION

Bromodomains refer to conserved protein structural folds which bind to N-acetylated lysine residues that are found in some proteins. The BET family of bromodomain containing proteins is comprised of four members (BRD2, BRD3, BRD4 and BRDt). Each member of the BET family employs two bromodomains to recognize N-acetylated lysine residues found primarily, but not exclusively, on the amino-terminal tails of histone proteins. These interactions modulate gene expression by recruiting transcription factors to specific genome locations within chromatin. For example, histone-bound BRD4 recruits the transcription factor P-TEFb to promoters, resulting in the expression of a subset of genes involved in cell cycle progression (Yang et al., Mol. Cell. Biol. 28: 967-976 (2008)). BRD2 and BRD3 also function as transcriptional regulators of growth promoting genes (LeRoy et al., Mol. Cell. 30: 51-60 (2008)). BET family members were recently established as being important for the maintenance of several cancer types (Zuber et al., Nature 478: 524-528 (2011); Mertz et al; Proc. Nat'l. Acad. Sci. 108: 16669-16674 (2011); Delmore et al., Cell 146: 1-14, (2011); Dawson et al., Nature 478: 529-533 (2011)). BET family members have also been implicated in mediating acute inflammatory responses through the canonical NF-KB pathway (Huang et al., Mol. Cell. Biol. 29: 1375-1387 (2009)) resulting in the upregulation of genes associated with the production of cytokines (Nicodeme et al., Nature 468: 1119-1123, (2010)). Suppression of cytokine induction by BET bromodomain inhibitors has been shown to be an effective approach to treat inflammation-mediated kidney disease in an animal model (Zhang, et al., J. Biol. Chem. 287: 28840-28851 (2012)). BRD2 function has been linked to predisposition for dyslipidemia or improper regulation of adipogenesis, elevated inflammatory profiles and increased susceptibility to autoimmune diseases (Denis, Discovery Medicine 10: 489-499 (2010)). The human immunodeficiency virus utilizes BRD4 to initiate transcription of viral RNA from stably integrated viral DNA (Jang et al., Mol. Cell, 19: 523-534 (2005)). Treatment of db/db mice with a BET specific bromodomain inhibitor has been shown to attenuate proteinuria, thus providing a potential new treatment for diabetic nephropathy (Liu, et al., "Role of Transcription Factor Acetylation in Diabetic Kidney Disease" Diabetes, DOI: 10.2337/db13-1810 (2014)). BET bromodomain inhibitors have also been shown to reactivate HIV transcription in models of latent T cell infection and latent monocyte infection (Banerjee, et al, J. Leukocyte Biol. 92(6): 1147-1154 (2012)). BRDt has an important role in spermatogenesis that is blocked by BET bromodomain inhibitors (Matzuk, et al., Cell 150: 673-684 (2012)). Studies with BET inhibitors have demonstrated proof-of-concept efficacy in animal models of sepsis and endotoxic shock (Nicodeme, et al., Nature 468: 1119-1123 (2010)), insulin resistance and hepatic steatosis (Bradner, et al., Composition and methods for modulating metabolism. WO2011/143651A1), idiopathic pulmonary fibrosis (Tang, et l., Am. J. Pathol. 183: 470-479 (2013)) and heart failure (Spiltoir, et al., J. Mol. Cellular. Cardiol. 63: 175-179 (2013), Anand, et al., Cell 154: 569-582 (2013)). Accordingly, there is an ongoing medical need to develop new drugs and crystalline forms thereof to treat these indications.

SUMMARY

Figure 1:
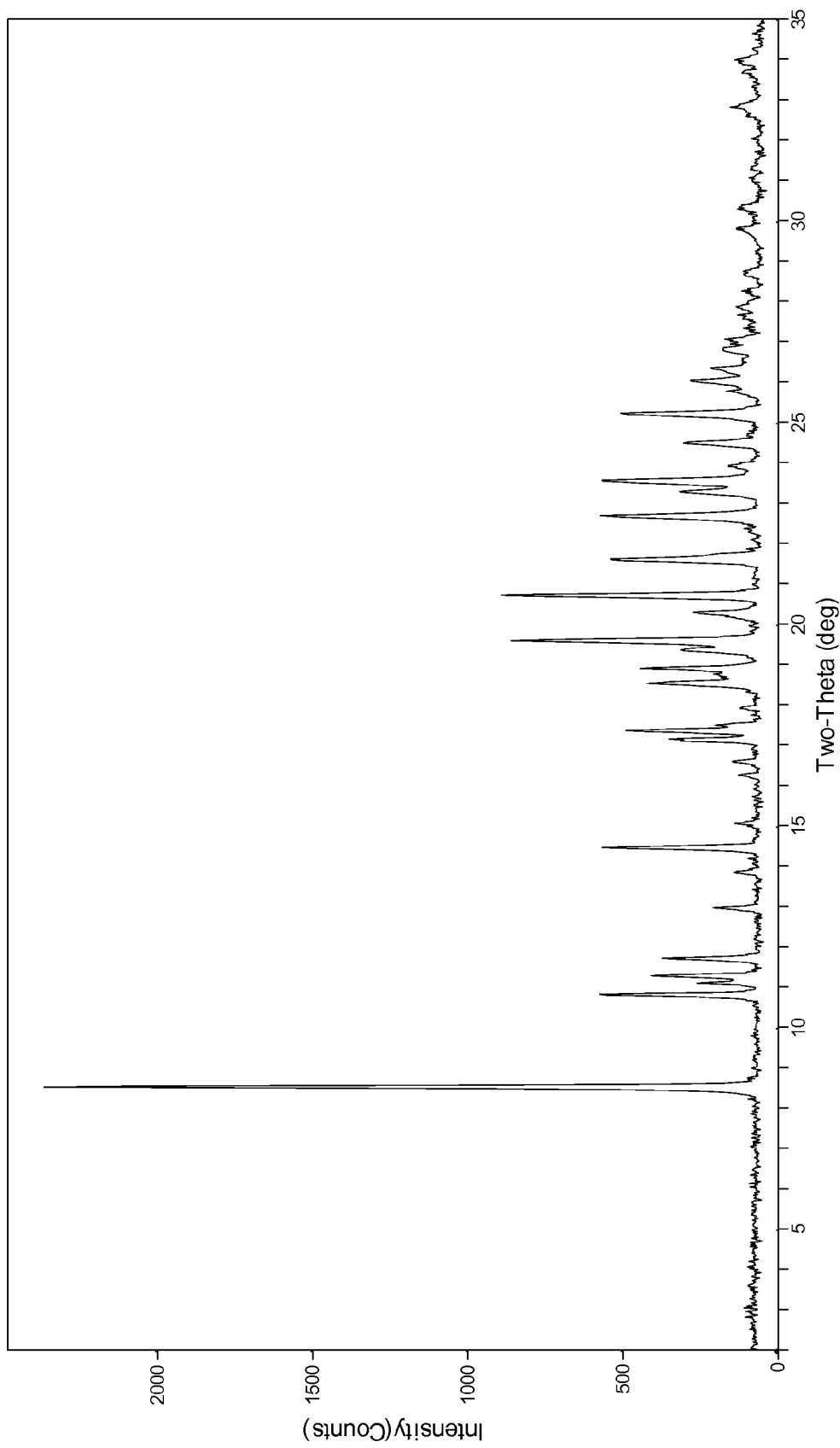
FIG. 1 provides a powder X-ray diffraction (PXRD) scan of N-[4-(2,4-difluorophenoxy)-3-(6-methyl-7-oxo-6,7-dihydro-1H-pyrrolo[2,3-c]pyridin-4-yl)phenyl]ethanesulfonamide Form I.

In one aspect the present invention relates to an isolated crystalline form of N-[4-(2,4-difluorophenoxy)-3-(6-methyl-7-oxo-6,7-dihydro-1H-pyrrolo[2,3-c]pyridin-4-yl)phenyl]ethanesulfonamide, wherein the crystalline form has a powder X-ray diffraction pattern comprising three or more 2θ peak values ±0.2 selected from the group consisting of: 6.2°, 9.0°, 12.3°, 12.6°, 15.6°, 22.1°, 25.6°, 26.3°, 27.0°, and 27.3°. In one aspect the present invention relates to an isolated crystalline form of N-[4-(2,4-difluorophenoxy)-3-(6-methyl-7-oxo-6,7-dihydro-1H-pyrrolo[2,3-c]pyridin-4-yl)phenyl]ethanesulfonamide, wherein the crystalline form has a powder X-ray diffraction pattern comprising the following 2θ peak values ±0.2: 6.2°, 9.0°, 12.3°, 12.6°, 15.6°, 22.1°, 25.6°, 26.3°, 27.0°, and 27.3°. In certain embodiments, the powder X-ray diffraction pattern comprises the following 2θ peak values ±0.2: 6.2°, 9.0°, 11.0°, 12.3°, 12.6°, 13.1°, 14.1°, 15.6°, 16.4°, 16.5°, 16.9°, 17.8°, 18.1°, 18.3°, 18.9°, 20.4°, 21.1°, 21.6°, 21.8°, 22.1°, 22.9°, 23.2°, 24.4°, 24.7°, 25.6°, 26.3°, 27.0°, and 27.3°. In certain embodiments, the powder X-ray diffraction pattern comprises three, four, five, or six 2θ peak values ±0.2 selected from the group consisting of 6.2°, 9.0°, 12.3°, 12.6, 15.6°, 22.1°, 25.6°, 26.3°, 27.0°, and 27.3°. In certain embodiments, the powder X-ray diffraction pattern comprises six 2θ peak values ±0.2 selected from the group consisting of 6.2°, 9.0°, 12.3°, 12.6, 15.6°, 22.1°, 25.6°, 26.3°, 27.0°, and 27.3°. In certain embodiments, the powder X-ray diffraction pattern comprises five 2θ peak values ±0.2 selected from the group consisting of 6.2°, 9.0°, 12.3°, 12.6, 15.6°, 22.1°, 25.6°, 26.3°, 27.0°, and 27.3°. In certain embodiments, the powder X-ray diffraction pattern comprises four 2θ peak values ±0.2 selected from the group consisting of 6.2°, 9.0°, 12.3°, 12.6, 15.6°, 22.1°, 25.6°, 26.3°, 27.0°, and 27.3°. In certain embodiments, the powder X-ray diffraction pattern comprises three 2θ peak values ±0.2 selected from the group consisting of 6.2°, 9.0°, 12.3°, 12.6, 15.6°, 22.1°, 25.6°, 26.3°, 27.0°, and 27.3°. In certain embodiments, the powder X-ray diffraction pattern comprises the following 2θ peak values ±0.2: 6.2°, 9.0°, 12.3°, 12.6, 15.6°, 22.1°, 25.6°, 26.3°, 27.0°, and 27.3°. In certain embodiments, the powder X-ray diffraction pattern comprises the following 2θ peak values ±0.2: 6.2°, 9.0°, 12.3°, 12.6°, and 15.6°. In certain embodiments, the powder X-ray diffraction pattern comprises the following 2θ peak values ±0.2: 22.1°, 25.6°, 26.3°, 27.0°, and 27.3°. In certain embodiments, the powder X-ray diffraction pattern comprises peak values ±0.2 at 2θ positions 6.2°, 9.0°, 12.3°, 12.6°, 13.1°, 14.1°, 16.4°, 16.5°, 16.9°, 17.8°, 18.1°, 18.3°, and 18.9°. In certain embodiments, the powder X-ray diffraction pattern comprises peak values ±0.2 at 2θ positions 6.2°, 9.0°, 12.3°, 12.6°, 13.1°, 14.1°, 18.1°, and 18.9°. In certain embodiments, the powder X-ray diffraction pattern comprises peak values ±0.2 at 2θ positions 6.2°, 9.0°, 12.3°, 12.6°, 13.1°, and 18.1°. In certain embodiments, the powder X-ray diffraction pattern comprises peak values ±0.2 at 2θ positions 9.0°, 12.3°, 12.6°, 13.1°, and 18.1°. In certain embodiments, crystalline form II has a differential scanning calorimetry thermogram endotherm between 240 and 242° C. In certain embodiments, crystalline form II has a differential scanning calorimetry thermogram endotherm at approximately 241° C. In certain embodiments, the endotherm is determined using DSC at a heating rate of 10° C./min. In certain embodiments, the powder X-ray diffraction pattern comprises peak values ±0.2 at 2θ positions 6.2°, 9.0°, 11.0°, 12.2°, 12.6°, 13.1°, 14.1°, 15.5°, 16.3°, 16.5°, 16.9°, 17.8°, 18.0°, 18.3°, 18.9°, 20.4°, 21.0°, 21.6°, 21.8°, 22.1°, 22.9°, 23.2°, 24.4°, 24.6°, 25.5°, 26.3°, 26.9°, and 27.2. In certain embodiments, the powder X-ray diffraction pattern comprises peak values ±0.2 at 2θ positions ±0.2 selected from the group consisting of: 6.2°, 9.0°, 12.2°, 12.6°, 15.5°, 22.1°, 25.5°, 26.3°, 26.9°, and 27.2°.

In another aspect the present invention relates to pharmaceutical compositions comprising crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide, and at least one pharmaceutically acceptable carrier. In certain embodiments, the pharmaceutical composition is a solid dosage form.

In another aspect the present invention relates to methods for treating cancer in a subject comprising administering a therapeutically effective amount of a pharmaceutical composition comprising crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide and at least one pharmaceutically acceptable carrier, to a subject in need thereof. In certain embodiments, the cancer is selected from the group consisting of: acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenström's macroglobulinemia, testicular tumors, uterine cancer and Wilms' tumor. In certain embodiments, the method further comprises administering a therapeutically effective amount of at least one additional therapeutic agent. In certain embodiments, the additional therapeutic agent is selected from the group consisting of cytarabine, bortezomib, and 5-azacitidine.

In another aspect, the present invention relates to a method of treating a disease or condition in a subject comprising administering a therapeutically effective amount of a crystalline Form II of N-[4-(2,4-difluorophenoxy)-3-(6-methyl-7-oxo-6,7-dihydro-1H-pyrrolo[2,3-c]pyridin-4-yl)phenyl]ethanesulfonamide to a subject in need thereof, wherein said disease or condition is selected from the group consisting of: Addison's disease, acute gout, ankylosing spondylitis, asthma, atherosclerosis, Behcet's disease, bullous skin diseases, cardiac myopathy, cardiac hypertrophy, chronic obstructive pulmonary disease (COPD), Crohn's disease, dermatitis, eczema, giant cell arteritis, glomerulonephritis, heart failure, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis. In certain embodiments, the method further comprises administering a therapeutically effective amount of at least one additional therapeutic agent.

In another aspect, the present invention relates to a method of treating a chronic kidney disease or condition in a subject comprising administering a therapeutically effective amount of a crystalline Form II of N-[4-(2,4-difluorophenoxy)-3-(6-methyl-7-oxo-6,7-dihydro-1H-pyrrolo[2,3-c]pyridin-4-yl)phenyl]ethanesulfonamide to a subject in need thereof, wherein said disease or condition is selected from the group consisting of: diabetic nephropathy, hypertensive nephropathy, HIV-associated nephropathy, glomerulonephritis, lupus nephritis, IgA nephropathy, focal segmental glomerulosclerosis, membranous glomerulonephritis, minimal change disease, polycystic kidney disease and tubular interstitial nephritis. In certain embodiments, the method further comprises administering a therapeutically effective amount of at least one additional therapeutic agent.

In another aspect, the present invention relates to a method of treating an acute kidney injury or disease or condition in a subject comprising administering a therapeutically effective amount of a crystalline Form II of N-[4-(2,4-difluorophenoxy)-3-(6-methyl-7-oxo-6,7-dihydro-1H-pyrrolo[2,3-c]pyridin-4-yl)phenyl]ethanesulfonamide to a subject in need thereof, wherein said acute kidney injury or disease or condition is selected from the group consisting of: ischemia-reperfusion induced kidney disease, cardiac and major surgery induced kidney disease, percutaneous coronary intervention induced kidney disease, radio-contrast agent induced kidney disease, sepsis induced kidney disease, pneumonia induced kidney disease, and drug toxicity induced kidney disease. In certain embodiments, the method further comprises administering a therapeutically effective amount of at least one additional therapeutic agent.

In another aspect, the present invention relates to methods of treating AIDS in a subject comprising administering a therapeutically effective amount of a crystalline Form II of N-[4-(2,4-difluorophenoxy)-3-(6-methyl-7-oxo-6,7-dihydro-1H-pyrrolo[2,3-c]pyridin-4-yl)phenyl]ethanesulfonamide to a subject in need thereof. In certain embodiments, the method further comprises administering a therapeutically effective amount of at least one additional therapeutic agent.

In another aspect, the present invention relates to a method of treating obesity, dyslipidemia, hypercholesterolemia, Alzheimer's disease, metabolic syndrome, hepatic steatosis, type II diabetes, insulin resistance, diabetic retinopathy or diabetic neuropathy in a subject comprising administering a therapeutically effective amount of a crystalline Form II of N-[4-(2,4-difluorophenoxy)-3-(6-methyl-7-oxo-6,7-dihydro-1H-pyrrolo[2,3-c]pyridin-4-yl)phenyl]ethanesulfonamide to a subject in need thereof. In certain embodiments, the method further comprises administering a therapeutically effective amount of at least one additional therapeutic agent.

In another aspect, the present invention relates to a methods of contraception in a male subject comprising administering a therapeutically effective amount of a crystalline Form II of N-[4-(2,4-difluorophenoxy)-3-(6-methyl-7-oxo-6,7-dihydro-1H-pyrrolo[2,3-c]pyridin-4-yl)phenyl]ethanesulfonamide to a subject in need thereof. In certain embodiments, the method further comprises administering a therapeutically effective amount of at least one additional therapeutic agent.

A further aspect of the invention provides the use of a crystalline Form II of N-[4-(2,4-difluorophenoxy)-3-(6-methyl-7-oxo-6,7-dihydro-1H-pyrrolo[2,3-c]pyridin-4-yl)phenyl]ethanesulfonamide, alone or in combination with at least one additional therapeutic agent, in the manufacture of a medicament for treating or preventing conditions and disorders disclosed herein, with or without a pharmaceutically acceptable carrier.

In certain embodiments, the invention provides the use of a crystalline Form II of N-[4-(2,4-difluorophenoxy)-3-(6-methyl-7-oxo-6,7-dihydro-1H-pyrrolo[2,3-c]pyridin-4-yl)phenyl]ethanesulfonamide, alone or in combination with at least one additional therapeutic agent, in the manufacture of a medicament for treating cancer, with or without a pharmaceutically acceptable carrier.

As mentioned above, crystalline Form II of N-[4-(2,4-difluorophenoxy)-3-(6-methyl-7-oxo-6,7-dihydro-1H-pyrrolo[2,3-c]pyridin-4-yl)phenyl]ethanesulfonamide may provide advantages in formulating pharmaceutical compositions. Accordingly, one aspect of the present invention relates to a pharmaceutical composition comprising the N-[4-(2,4-difluorophenoxy)-3-(6-methyl-7-oxo-6,7-dihydro-1H-pyrrolo[2,3-c]pyridin-4-yl)phenyl]ethanesulfonamide in crystalline form, and a pharmaceutically acceptable carrier. In a further embodiment, the composition according to the present invention comprises N-[4-(2,4-difluorophenoxy)-3-(6-methyl-7-oxo-6,7-dihydro-1H-pyrrolo[2,3-c]pyridin-4-yl)phenyl]ethanesulfonamide Form II as described above, alone or in combination with a second therapeutic agent, and a pharmaceutically acceptable carrier.

Another aspect relates to a process for preparing crystalline Form II of N-[4-(2,4-difluorophenoxy)-3-(6-methyl-7-oxo-6,7-dihydro-1H-pyrrolo[2,3-c]pyridin-4-yl)phenyl]ethanesulfonamide.

In another aspect the present invention relates to methods of making a pharmaceutical composition comprising N-[4-(2,4-difluorophenoxy)-3-(6-methyl-7-oxo-6,7-dihydro-1H-pyrrolo[2,3-c]pyridin-4-yl)phenyl]ethanesulfonamide and a pharmaceutically acceptable carrier, comprising: mixing an isolated crystalline form of N-[4-(2,4-difluorophenoxy)-3-(6-methyl-7-oxo-6,7-dihydro-1H-pyrrolo[2,3-c]pyridin-4-yl)phenyl]ethanesulfonamide, wherein the crystalline form has a powder X-ray diffraction pattern comprising three or more 2θ peak values ±0.2 selected from the group consisting of: 6.2°, 9.0°, 12.3°, 12.6°, 15.6°, 22.1°, 25.6°, 26.3°, 27.0°, and 27.3°, with a pharmaceutically acceptable carrier.

In another aspect the present invention relates to compositions comprising greater than 90% (w/w) crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide, wherein the crystalline form has a powder X-ray diffraction pattern comprising three or more 2θ peak values ±0.2 selected from the group consisting of: 6.2°, 9.0°, 12.3°, 12.6°, 15.6°, 22.1°, 25.6°, 26.3°, 27.0°, and 27.3°. In certain embodiments, the composition comprises between 90-99% (w/w) crystalline form II.

DETAILED DESCRIPTION

N-[4-(2,4-difluorophenoxy)-3-(6-methyl-7-oxo-6,7-dihydro-1H-pyrrolo[2,3-c]pyridin-4-yl)phenyl]ethanesulfonamide can be prepared as a crystalline form which is termed crystalline Form II. As used herein, a crystalline form of a compound refers to the same chemical entity, but in a different crystalline arrangement. N-[4-(2,4-difluorophenoxy)-3-(6-methyl-7-oxo-6,7-dihydro-1H-pyrrolo[2,3-c]pyridin-4-yl)phenyl]ethanesulfonamide is an inhibitor of human BRD4, and of the proliferation of the breast cancer cell line MX-1.

It is noted that, as used in this specification and the intended claims, the singular form "a," "an," and "the" include plural referents unless the context clearly dictates otherwise. Thus, for example, reference to "a compound" includes a single compound as well as one or more of the same or different compounds, reference to "a pharmaceutically acceptable carrier" refers to a single pharmaceutically acceptable carrier as well as one or more pharmaceutically acceptable carriers, and the like.

When used in reference to crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide, which is greater than about 90% pure. This means that the N-[4-(2,4-difluorophenoxy)-3-(6-methyl-7-oxo-6,7-dihydro-1H-pyrrolo[2,3-c]pyridin-4-yl)phenyl]ethanesulfonamide crystal form II does not contain more than about 10% of any other compound and, in particular, does not contain more than about 10% of crystal form I. More preferably, the term "substantially pure" refers to crystalline Form II, which is greater than about 95% pure. This means that crystalline Form II does not contain more than about 5% of any other compound and, in particular, does not contain more than about 5% of crystalline Form I. Even more preferably, the term "substantially pure" refers to crystalline Form II, which is greater than about 97% pure. This means that crystalline Form II does not contain more than about 3% of any other compound, and, in particular, does not contain more than about 3% of crystalline Form I.

The crystalline Form I of N-[4-(2,4-difluorophenoxy)-3-(6-methyl-7-oxo-6,7-dihydro-1H-pyrrolo[2,3-c]pyridin-4-yl)phenyl]ethanesulfonamide may also be referred to as "Form I of N-[4-(2,4-difluorophenoxy)-3-(6-methyl-7-oxo-6,7-dihydro-1H-pyrrolo[2,3-c]pyridin-4-yl)phenyl]ethanesulfonamide," or by similar expressions, and is having the physiochemical parameters outlined herein. The crystalline Form II of N-[4-(2,4-difluorophenoxy)-3-(6-methyl-7-oxo-6,7-dihydro-1H-pyrrolo[2,3-c]pyridin-4-yl)phenyl]ethanesulfonamide may also be referred to as "Form II of N-[4-(2,4-difluorophenoxy)-3-(6-methyl-7-oxo-6,7-dihydro-1H-pyrrolo[2,3-c]pyridin-4-yl)phenyl]ethanesulfonamide," or by similar terms, and is having the physiochemical parameters outlined herein.

In certain aspects, the present invention further relates to a pharmaceutical composition comprising N-[4-(2,4-difluorophenoxy)-3-(6-methyl-7-oxo-6,7-dihydro-1H-pyrrolo[2,3-c]pyridin-4-yl)phenyl]ethanesulfonamide Form II and a pharmaceutically acceptable carrier.

The crystalline forms of N-[4-(2,4-difluorophenoxy)-3-(6-methyl-7-oxo-6,7-dihydro-1H-pyrrolo[2,3-c]pyridin-4-yl)phenyl]ethanesulfonamide, for example Form II, can be useful as an active pharmaceutical ingredient (API) in the preparation of pharmaceutical compositions suitable for any route of administration, including oral, to a subject in need thereof. Other routes of administration include, without limitation, parenteral, sublingual, buccal, intranasal, pulmonary, topical, transdermal, intradermal, ocular, otic, rectal, vaginal, intragastric, intracranial, intrasynovial and intra-articular routes.

N-[4-(2,4-difluorophenoxy)-3-(6-methyl-7-oxo-6,7-dihydro-1H-pyrrolo[2,3-c]pyridin-4-yl)phenyl]ethanesulfonamide is present in a pharmaceutical composition of the invention in an amount that can be therapeutically effective when the composition is administered to a subject in need thereof according to an appropriate regimen. Typically, a unit dose (the amount administered at a single time), which can be administered at an appropriate frequency, e.g., twice daily to once weekly, is about 10 to about 1,000 mg, depending on the compound in question. Where frequency of administration is once daily (q.d.), unit dose and daily dose are the same. Illustratively, the unit dose is typically about 25 to about 1,000 mg, more typically about 50 to about 500 mg, for example about 50, about 100, about 150, about 200, about 250, about 300, about 350, about 400, about 450 or about 500 mg.

The term "pharmaceutically acceptable carrier" as used herein, means a non-toxic, inert solid, semi-solid or liquid filler, diluent, encapsulating material or formulation auxiliary of any type. Pharmaceutically acceptable carriers include but are not limited to, for example, encapsulating materials and additives such as absorption accelerators, antioxidants, binders, buffers, carriers, coating agents, coloring agents, diluents, disintegrating agents, emulsifiers, extenders, fillers, flavoring agents, glidants, humectants, lubricants, perfumes, preservatives, propellants, releasing agents, sterilizing agents, sweeteners, solubilizers, wetting agents, mixtures thereof and the like.

Pharmaceutically acceptable carriers for the preparation of formulations comprising or made with crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide to be administered orally in solid dosage form include, for example, agar, alginic acid, aluminum hydroxide, benzyl alcohol, benzyl benzoate, 1,3-butylene glycol, carbomers, castor oil, cellulose, cellulose acetate, cocoa butter, copovidone, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl cellulose, isopropanol, isotonic saline, lactose, magnesium hydroxide, magnesium stearate, malt, mannitol, monoglycerides, olive oil, povidone, peanut oil, potassium phosphate salts, potato starch, povidone, propylene glycol, Ringer's solution, safflower oil, sesame oil, silicon dioxide, sodium carboxymethyl cellulose, sodium phosphate salts, sodium lauryl sulfate, sodium sorbitol, sodium stearylfumarate, soybean oil, stearic acids, stearyl fumarate, sucrose, surfactants, talc, tragacanth, tetrahydrofurfuryl alcohol, triglycerides, vitamin E and derivatives thereof, water, mixtures thereof and the like.

Pharmaceutically acceptable carriers for the preparation of formulations comprising or made with crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide to be administered ophthalmically or orally in liquid dosage forms include, for example, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water, mixtures thereof and the like.

Pharmaceutically acceptable carriers for the preparation of formulations comprising or made with crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide to be administered osmotically include, for example, chlorofluorohydrocarbons, ethanol, water, mixtures thereof and the like.

Pharmaceutically acceptable carriers for the preparation of formulations comprising or made with crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide to be administered parenterally include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water, mixtures thereof and the like.

Pharmaceutically acceptable carriers for the preparation of formulations comprising or made with crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide to be administered rectally or vaginally include, but are not limited to, cocoa butter, polyethylene glycol, wax, mixtures thereof and the like.

The composition is normally administered in an amount providing a therapeutically effective daily dose of the drug. The term "daily dose" herein means the amount of drug administered per day, regardless of the frequency of administration. For example, if the subject receives a unit dose of 150 mg twice daily, the daily dose is 300 mg. Use of the term "daily dose" will be understood not to imply that the specified dosage amount is necessarily administered once daily. However, in a particular embodiment the dosing frequency is once daily (q.d.), and the daily dose and unit dose in this embodiment are the same.

What constitutes a therapeutically effective dose depends on the particular compound, the subject (including species and body weight of the subject), the disease (e.g., the particular type of cancer) to be treated, the stage and/or severity of the disease, the individual subject's tolerance of the compound, whether the compound is administered in monotherapy or in combination with one or more other drugs, e.g., other chemotherapeutics for treatment of cancer, and other factors. Thus the daily dose can vary within wide margins, for example from about 10 to about 1,000 mg. Greater or lesser daily doses may be appropriate in specific situations. It will be understood that recitation herein of a "therapeutically effective" dose herein does not necessarily require that the drug be therapeutically effective if only a single such dose is administered; typically therapeutic efficacy depends on the composition being administered repeatedly according to a regimen involving appropriate frequency and duration of administration. A suitable therapeutically effective dose can be selected by the physician of ordinary skill without undue experimentation. The physician may, for example, start a cancer patient on a course of therapy with a relatively low daily dose and titrate the dose upwards over a period of days or weeks, to reduce risk of adverse side-effects.

Illustratively, suitable doses of N-[4-(2,4-difluorophenoxy)-3-(6-methyl-7-oxo-6,7-dihydro-1H-pyrrolo[2,3-c]pyridin-4-yl)phenyl]ethanesulfonamide are generally about 10 to about 1,000 mg/day, more typically about 50 to about 500 mg/day or about 200 to about 400 mg/day, for example about 50, about 100, about 150, about 200, about 250, about 300, about 350, about 400, about 450 or about 500 mg/day, administered at an average dosage interval of 3 to 10 days, or about 4 to 8 days, or about 7 days.

A composition comprising crystalline N-[4-(2,4-difluorophenoxy)-3-(6-methyl-7-oxo-6,7-dihydro-1H-pyrrolo[2,3-c]pyridin-4-yl)phenyl]ethanesulfonamide Form II suitable for use in monotherapy or in combination therapy, for example with other chemotherapeutics or with ionizing radiation.

Crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide, and pharmaceutical compositions comprising crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide, can be administered to a subject suffering from a bromodomain-mediated disorder or condition. The term "administering" refers to the method of contacting a compound with a subject. Thus, the crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide can be administered by injection, that is, intravenously, intramuscularly, intracutaneously, subcutaneously, intraduodenally, parentally, or intraperitoneally. It can also be administered by inhalation, for example, intranasally. Additionally, crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide can be administered transdermally, topically, via implantation, transdermally, topically, and via implantation. In certain embodiments, crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide may be delivered orally. In other embodiments, crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide can also be delivered rectally, bucally, intravaginally, ocularly, or by insufflation. Bromodomain-mediated disorders and conditions can be treated prophylactically, acutely, and chronically using a crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide, depending on the nature of the disorder or condition.

A "bromodomain-mediated disorder or condition" is characterized by the participation of one or more bromodomains (e.g., BRD4) in the inception, manifestation of one or more symptoms or disease markers, severity, or progression of a disorder or condition.

Accordingly, crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide may be used to treat cancer, including, but not limited to acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenström's macroglobulinemia, testicular tumors, uterine cancer and Wilms' tumor.

Further, crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide may be used to treat inflammatory diseases, inflammatory conditions, and autoimmune diseases, including, but not limited to: Addison's disease, acute gout, ankylosing spondylitis, asthma, atherosclerosis, Behcet's disease, bullous skin diseases, cardiac myopathy, cardiac hypertrophy, chronic obstructive pulmonary disease (COPD), Crohn's disease, dermatitis, eczema, giant cell arteritis, glomerulonephritis, heart failure, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis.

Crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide, may be used to treat AIDS.

Crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide, may be used to treat chronic kidney disease or condition including, but are not limited to: diabetic nephropathy, hypertensive nephropathy, HIV-associated nephropathy, glomerulonephritis, lupus nephritis, IgA nephropathy, focal segmental glomerulosclerosis, membranous glomerulonephritis, minimal change disease, polycystic kidney disease and tubular interstitial nephritis.

Crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide, may be used to treat acute kidney injury or disease or condition including, but are not limited to: ischemia-reperfusion induced, cardiac and major surgery induced, percutaneous coronary intervention induced, radiocontrast agent induced, sepsis induced, pneumonia induced, and drug toxicity induced.

Crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide, may be used to treat obesity, dyslipidemia, hypercholesterolemia, Alzheimer's disease, metabolic syndrome, hepatic steatosis, type II diabetes, insulin resistance, diabetic retinopathy or diabetic neuropathy.

Crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide, may be used to prevent conception by inhibiting spermatogenesis in a subject comprising administering a therapeutically effective amount of a crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide, to a subject in need thereof.

Crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide, can be co-administered to a subject. The term "co-administered" means the administration of two or more different pharmaceutical agents or treatments (e.g., radiation treatment) that are administered to a subject by combination in the same pharmaceutical composition or separate pharmaceutical compositions. Thus co-administration involves administration at the same time of a single pharmaceutical composition comprising two or more therapeutic agents or administration of two or more different compositions to the same subject at the same or different times.

Crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide can be co-administered with a therapeutically effective amount of one or more agents to treat a cancer, where examples of the agents include, such as radiation, alkylating agents, angiogenesis inhibitors, antibodies, antimetabolites, antimitotics, antiproliferatives, antivirals, aurora kinase inhibitors, apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs (dual variable domain antibodies), leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPB), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (bromodomain) inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and J. A. Trapani, J. of Immunology 1997, 158 (12), 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site. Multispecific DVDs include DVD binding proteins that bind DLL4 and VEGF, or C-met and EGFR or ErbB3 and EGFR.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(41R)-3-(dimethylamino)-1-((phenylsulfanyl)methyl) propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax), ABT-199, and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include EGFR antibodies, ABX-EGF, anti-EGFR immunoliposomes, EGF-vaccine, EMD-7200, ERBITUX® (cetuximab), HR3, IgA antibodies, IRESSA (gefitinib), TARCEVA (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FC1, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-0,1-vcMMAE, PSMA-ADC, MEDI-547, SGN-19 Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474), GA101, ofatumumab, ABT-806

(mAb-806), ErbB3 specific antibodies, BSG2 specific antibodies, DLL4 specific antibodies and C-met specific antibodies, and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirubicin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE,(IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® ($^{90}$Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofiran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide can also be used as radiosensitizers that enhance the efficacy of radiotherapy. Examples of radiotherapy include external beam radiotherapy, teletherapy, brachytherapy and sealed, unsealed source radiotherapy and the like.

Additionally, a crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide, may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly Cl$_2$U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine)(ONCOVIN®; P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EP0906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX®

(prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT®(AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECINT™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (Streptomyces staurospores), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

Crystalline form II of N-[4-(2,4-difluorophenoxy)-3-(6-methyl-7-oxo-6,7-dihydro-1H-pyrrolo[2,3-c]pyridin-4-yl) phenyl]ethanesulfonamide, can also be co-administered with a therapeutically effective amount of one or more therapeutic agents to treat an inflammatory disease or condition, or autoimmune disease, where examples of the agents include, such as methotrexate, tofacitinib, 6-mercaptopurine, azathioprine sulphasalazine, mesalazine, olsalazine chloroquinine/ hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g., NIK, IKK, p38 or MAP kinase inhibitors), IL-1β converting enzyme inhibitors, T-cell signalling inhibitors such as kinase inhibitors, metalloproteinase inhibitors, sulfasalazine, 6-mercaptopurines, angiotensin converting enzyme inhibitors, soluble cytokine receptors and derivatives thereof (e.g. soluble p55 or p75 TNF receptors and the derivatives p75TNFRIgG (etanercept) and p55TNFRIgG (Lenercept), sIL-1R1, sIL-1R11, sIL-6R), antiinflammatory cytokines (e.g. IL-4, IL-10, IL-11, IL-13 and TGFβ), celecoxib, folic acid, hydroxychloroquine sulfate, rofecoxib, etanercept, infliximab, adalimumab, certolizumab, tocilizumab, abatacept, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/ fa/pyridoxine, acetaminophen, alendronate sodium, prednisolone, cortisone, betamethasone, morphine sulfate, lidocaine hydrochloride, indomethacin, glucosamine sulf/ chondroitin, amitriptyline HCl, sulfadiazine, oxycodone HCl/acetaminophen, olopatadine HCl misoprostol, naproxen sodium, omeprazole, cyclophosphamide, rituximab, IL-1 TRAP, MRA, CTLA4-IG, IL-18 BP, anti-IL-12, Anti-ILLS, BIRB-796, SCIO-469, VX-702, AMG-548, VX-740, Roflumilast, IC-485, CDC-801, S1P1 agonists (such as FTY720), PKC family inhibitors (such as Ruboxistaurin or AEB-071) and Mesopram. In certain embodiments, combinations include methotrexate or leflunomide and in moderate or severe rheumatoid arthritis cases, cyclosporine and anti-TNF antibodies as noted above.

Non-limiting examples of therapeutic agents for inflammatory bowel disease with which crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide may be co-administered include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, TNF, LT, IL-1, IL-2, IL-6, IL-7, IL-8, IL-12, IL-15, IL-16, IL-23, EMAP-II, GM-CSF, FGF, and PDGF; cell surface molecules such as CD2, CD3, CD4, CD8, CD25, CD28, CD30, CD40, CD45, CD69, CD90 or their ligands; methotrexate; cyclosporine; FK506; rapamycin; mycophenolate mofetil; leflunomide; NSAIDs, for example, ibuprofen; corticosteroids such as prednisolone; phosphodiesterase inhibitors; adenosine agonists; antithrombotic agents; complement inhibitors; adrenergic agents; agents which interfere with signalling by proinflammatory cytokines such as TNFα or IL-1 (e.g. NIK, IKK, or MAP kinase inhibitors); IL-1β converting enzyme inhibitors; TNFα converting enzyme inhibitors; T-cell signalling inhibitors such as kinase inhibitors; metalloproteinase inhibitors; sulfasalazine; azathioprine; 6-mercaptopurines; angiotensin converting enzyme inhibitors; soluble cytokine receptors and derivatives thereof (e.g. soluble p55 or p75 TNF receptors, sIL-1R1, sIL-1R11, sIL-6R) and antiinflammatory cytokines (e.g. IL-4, IL-10, IL-11, IL-13 and TGFβ). Preferred examples of therapeutic agents for Crohn's disease with which a crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide can be combined include the following: TNF antagonists, for example, anti-TNF antibodies, D2E7 (adalimumab), CA2 (infliximab), CDP 571, TNFR-Ig constructs, (p75TNFRIgG (etanercept) and p55TNFRIgG (LENERCEPT™) inhibitors and PDE4 inhibitors. Crystalline form II of N-[4-(2,4-difluorophenoxy)-3-(6-methyl-7-oxo-6,7-dihydro-1H-pyrrolo[2, 3-c]pyridin-4-yl)phenyl]ethanesulfonamide can be combined with corticosteroids, for example, budenoside and dexamethasone; sulfasalazine, 5-aminosalicylic acid; olsalazine; and agents which interfere with synthesis or action of proinflammatory cytokines such as IL-1, for example, IL-1β converting enzyme inhibitors and IL-1ra; T cell signaling inhibitors, for example, tyrosine kinase inhibitors; 6-mercaptopurine; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrosewater; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma.

Non-limiting examples of therapeutic agents for multiple sclerosis with which a crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide, may be co-administered include the following: corticosteroids; prednisolone; methylprednisolone; azathioprine; cyclophosphamide; cyclosporine; methotrexate; 4-aminopyridine; tizanidine; interferon-β1a (AVONEX®; Biogen); interferon-(31b (BETASERON®; Chiron/Berlex); interferon α-n3) (Interferon Sciences/Fujimoto), interferon-α (Alfa Wassermann/J&J), interferon β1A-1F (Serono/Inhale Therapeutics), Peginterferon α 2b (Enzon/Schering-Plough), Copolymer 1 (Cop-1; COPAXONE®; Teva Pharmaceutical Industries, Inc.); hyperbaric oxygen; intravenous immunoglobulin; cladribine; antibodies to or antagonists of other human cytokines or growth factors and their receptors, for example, TNF, LT, IL-1, IL-2, IL-6, IL-7, IL-8, IL-12, IL-23, IL-15, IL-16, EMAP-II, GM-CSF, FGF, and PDGF. crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide can be combined with antibodies to cell surface molecules such as CD2, CD3, CD4, CD8, CD19, CD20, CD25, CD28, CD30, CD40, CD45, CD69, CD80, CD86, CD90 or their ligands. Crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide may also be combined with agents such as methotrexate, cyclosporine, FK506, rapamycin, mycophenolate mofetil, leflunomide, an S1P1 agonist, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g., NIK, IKK, p38 or MAP kinase inhibitors), IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1R1, sIL-1R11, sIL-6R) and antiinflammatory cytokines (e.g. IL-4, IL-10, IL-13 and TGFβ).

Crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide may also be co-administered with agents, such as alemtuzumab, dronabinol, daclizumab, mitoxantrone, xaliproden hydrochloride, fampridine, glatiramer acetate, natalizumab, sinnabidol, α-immunokine NNSO₃, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists and IL-4 agonists.

Non-limiting examples of therapeutic agents for ankylosing spondylitis with which a crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide can be co-administered include the following: ibuprofen, diclofenac, misoprostol, naproxen, meloxicam, indomethacin, diclofenac, celecoxib, rofecoxib, sulfasalazine, methotrexate, azathioprine, minocyclin, prednisone, and anti-TNF antibodies, D2E7 (HUMIRA®), CA2 (infliximab), CDP 571, TNFR-Ig constructs, (p75TNFRIgG (ENBREL) and p55TNFRIgG (LENERCEPT®).

Non-limiting examples of therapeutic agents for asthma with which a crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide, may be co-administered include the following: albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin HCl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine HCl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, anti-IL-13 antibody, and metaproterenol sulfate.

Non-limiting examples of therapeutic agents for COPD with which a crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide, may be co-administered include the following: albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, cilomilast and roflumilast.

Non-limiting examples of therapeutic agents for psoriasis with which a crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide may be co-administered include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine, ABT-874 and ustekinamab.

Non-limiting examples of therapeutic agents for psoriatic arthritis with which a crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide may be co-administered include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, D2E7 (adalimumab), and efalizumab.

Examples of therapeutic agents for SLE (Lupus) with which a crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide may be co-administered include the following: NSAIDS, for example, diclofenac, naproxen, ibuprofen, piroxicam, indomethacin; COX2 inhibitors, for example, celecoxib, rofecoxib, valdecoxib; anti-malarials, for example, hydroxychloroquine; steroids, for example, prednisone, prednisolone, budenoside, dexamethasone; cytotoxics, for example, azathioprine, cyclophosphamide, mycophenolate mofetil, methotrexate; inhibitors of PDE4 or purine synthesis inhibitor, for example Cellcept®. Crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide may also be combined with agents such as sulfasalazine, 5-aminosalicylic acid, olsalazine, Imuran® and agents which interfere with synthesis, production or action of proinflammatory cytokines such as IL-1, for example, caspase inhibitors like IL-1β converting enzyme inhibitors and IL-1ra. Crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide may also be used with T cell signaling inhibitors, for example, tyrosine kinase inhibitors; or molecules that target T cell activation molecules, for example, CTLA-4-IgG or anti-B7 family antibodies, anti-PD-1 family antibodies. Crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide can be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. Crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide may also be used with LJP 394 (abetimus), agents that deplete or inactivate B-cells, for example, Rituximab (anti-CD20 antibody), lymphostat-B (anti-B1yS antibody), TNF antagonists, for example, anti-TNF antibodies, D2E7 (adalimumab), CA2 (infliximab), CDP 571, TNFR-Ig constructs, (p75TNFRIgG (etanercept) and p55TNFRIgG (LENERCEPT™).

Crystalline form II of N-[4-(2,4-difluorophenoxy)-3-(6-methyl-7-oxo-6,7-dihydro-1H-pyrrolo[2,3-c]pyridin-4-yl) phenyl]ethanesulfonamide can also be co-administered with a therapeutically effective amount of one or more agents used in the prevention or treatment of AIDS, where examples of the agents include, HIV reverse transcriptase inhibitors, HIV protease inhibitors, immunomodulators, and other retroviral drugs. Examples of reverse transcriptase inhibitors include, but are not limited to, abacavir, adefovir, didanosine, dipivoxil delavirdine, efavirenz, emtricitabine, lamivudine, nevirapine, rilpivirine, stavudine, tenofovir, zalcitabine, and zidovudine. Examples of protease inhibitors include, but are not limited to, amprenavir, atazanavir, darunavir, indinavir, fosamprenavir, lopinavir, nelfinavir, ritonavir, saquinavir, and tipranavir. Examples of other retroviral drugs include, but are not limited to, elvitegravir, enfuvirtide, maraviroc and raltegravir.

Crystalline form II of N-[4-(2,4-difluorophenoxy)-3-(6-methyl-7-oxo-6,7-dihydro-1H-pyrrolo[2,3-c]pyridin-4-yl) phenyl]ethanesulfonamide can be co-administered with a therapeutically effective amount of one or more therapeutic agents to prevent or treat type II diabetes, hepatic steatosis, insulin resistance, metabolic syndrome and related disorders, where examples of the agents include, but are not limited to, insulin and insulins that have been modified to improve the duration of action in the body; agents that stimulate insulin secretion such as acetohexamide, chlorpropamide, glyburide, glimepiride, glipizide, glicazide, glycopyramide, gliquidone, rapaglinide, nataglinide, tolazamide and tolbutamide; agents that are glucagon-like peptide agonists such as exanatide, liraglutide and taspoglutide; agents that inhibit dipeptidyl-peptidase IV such as vildagliptin, sitagliptin, saxagliptin, linagliptin, allogliptin and septagliptin; agents that bind to the peroxisome proliferator-activated receptor gamma such as rosiglitazone and pioglitazone; agents that decrease insulin resistance such as metformin; agents that reduce glucose absorbance in the small intestine such as acarbose, miglitol and voglibose.

Crystalline form II of N-[4-(2,4-difluorophenoxy)-3-(6-methyl-7-oxo-6,7-dihydro-1H-pyrrolo[2,3-c]pyridin-4-yl) phenyl]ethanesulfonamide can be co-administered with a therapeutically effective amount of one or more therapeutic agents to prevent or treat acute kidney disorders and chronic kidney diseases, where examples of the agents include, but are not limited to, dopamine, diuretics such as furosemide, bumetanide, thiazide and the like, mannitol, calcium gluconate, sodium bicarbonate, albuterol, paricalcitol, doxercalciferol, cinacalcet and bardoxalone methyl.

The terms "treat", "treating", and "treatment" refer to a method of alleviating or abrogating a disease and/or its attendant symptoms.

The terms "prevent", "preventing", and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The phrase "therapeutically effective amount" means an amount of a compound, or a pharmaceutically acceptable salt thereof, sufficient to prevent the development of or to alleviate to some extent one or more of the symptoms of the condition or disorder being treated when administered alone or in conjunction with another pharmaceutical agent or treatment in a particular subject or subject population. For example in a human or other mammal, a therapeutically effective amount can be determined experimentally in a laboratory or clinical setting, or may be the amount required by the guidelines of the United States Food and Drug Administration, or equivalent foreign agency, for the particular disease and subject being treated.

The term "subject" is defined herein to refer to animals such as mammals, including, but not limited to, primates (e.g., humans), cows, sheep, goats, horses, dogs, cats, rabbits, rats, mice and the like. In preferred embodiments, the subject is a human.

The following Examples may be used for illustrative purposes and should not be deemed to narrow the scope of the invention.

EXAMPLES

Powder X-ray Diffraction (PXRD)

PXRD data were collected using a G3000 diffractometer (Inel Corp., Artenay, France) equipped with a curved position sensitive detector and parallel beam optics. The diffractometer was operated with a copper anode tube (1.5 kW fine focus) at 40 kV and 30 mA. An incident beam germanium monochromater provided monochromatic radiation. The diffractometer was calibrated using the attenuated direct beam at one-degree intervals. Calibration was checked using a silicon powder line position reference standard (NIST 640c). The instrument was computer controlled using the Symphonix software (Inel Corp., Artenay, France) and the data was analyzed using the Jade software (version 9, Materials Data, Inc., Livermore, Calif.). The sample was loaded onto an aluminum sample holder and leveled with a glass slide. The sample was irradiated with copper $K\alpha_1$ X-rays with the X-ray tube operated at 40 kV and 30 mA.

Figure 4:
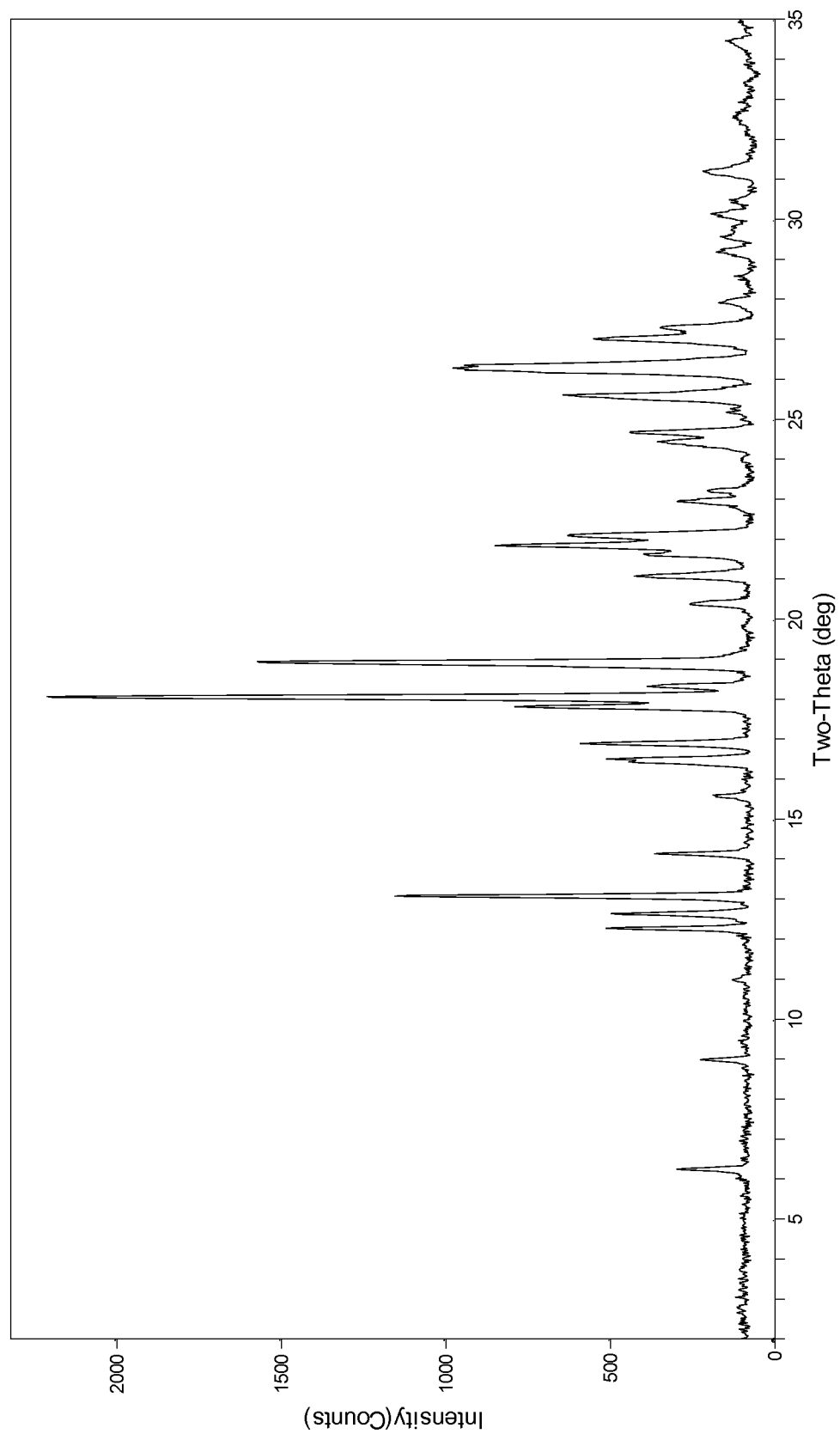
FIG. 4 provides a powder X-ray diffraction (PXRD) scan of N-[4-(2,4-difluorophenoxy)-3-(6-methyl-7-oxo-6,7-dihydro-1H-pyrrolo[2,3-c]pyridin-4-yl)phenyl]ethanesulfonamide Form II.

The PXRD patterns are shown in FIGS. 1 and 4. The Tables below include the analysis and are provided with the following approximate data: 2θ positions and relative intensity using peak height to measure height % (H %) in counts per second.

Differential Scanning calorimetry (DSC)

A DSC (Q-2000, TA Instruments, New Castle, Del.) equipped with Universal Analysis 2000 software (Version 4.5A, TA Instruments, New Castle, Del.) was used to determine the DSC thermal traces. The temperature axis was calibrated with biphenyl, indium, and tin standards. The cell constant was calibrated with indium. Unless otherwise stated, the sample (2-5 mg) was encapsulated in a ventilated aluminum pan, and heated at a rate of 10° C./min under a nitrogen gas flow of 50 mL/min during the study.

Thermal Gravimetric Analysis (TGA)

TGA traces were collected on a thermal balance (Q-500, TA Instruments, New Castle, Del.) equipped with a data analyzer (Universal Analysis 2000, version 4.5A, TA Instruments, New Castle, Del.). During experiments, the furnace was purged with nitrogen at 60 mL/min, while the balance chamber was purged at 40 mL/min. Temperature of the TGA furnace was calibrated using curie points of aluminum and nickel. Sample size ranged from 2 to 20 mg, and a heating rate of 10° C./min was used.

Preparation of N-[4-(2,4-difluorophenoxy)-3-(6-methyl-7-oxo-6,7-dihydro-1H-pyrrolo[2,3-c]pyridin-4-yl)phenyl]ethanesulfonamide Form I Step 1A A mixture of 2-bromo-1-fluoro-4-nitrobenzene (15 g, 68 mmol), 2,4-difluorophenol (7.82 mL, 82 mmol), and cesium carbonate (26.7 g, 82 mmol) in dimethylsulfoxide (75 mL) was heated at 110° C. for 1 hour. The reaction mixture was cooled to ambient temperature and water (1000 mL) and saturated aqueous sodium chloride (1000 mL) were added. The mixture was extracted with ethyl acetate (3×200 mL). The combined organics were washed with saturated aqueous sodium chloride, dried (anhydrous magnesium sulfate), filtered, and concentrated under reduced pressure to provide 2-bromo-1-(2,4-difluorophenoxy)-4-nitrobenzene (22.5 g, quantitative).

Step 2A

A mixture of 2-bromo-1-(2,4-difluorophenoxy)-4-nitrobenzene (22.5 g, 68.2 mmol), iron powder (19.04 g, 341 mmol), and ammonium chloride (7.30 g, 136 mmol) in tetrahydrofuran (117 mL), ethanol (117 mL), and water (39.0 mL) was heated under reflux at 100° C. for 2 hours. The reaction mixture was cooled to just below reflux temperature, filtered through Celite, and the filter cake washed with warm methanol (3×50 mL). The resulting solution was concentrated under reduced pressure and then neutralized to a pH of 8 with saturated sodium hydrogen carbonate (150 mL). The mixture was extracted with ethyl acetate (3×100 mL). The combined organics were washed with saturated aqueous sodium chloride, dried over anhydrous magnesium sulfate, filtered, and concentrated. The residue was purified by flash chromatography (silica gel, ethyl acetate/hexane gradient 0-15%) to provide 3-bromo-4-(2,4-difluorophenoxy)aniline (16.8 g, 82% yield).

Step 3A

5-Bromo-2-methoxy-4-methyl-3-nitropyridine (15.0 g, 60.7 mmol) was dissolved in dimethylformamide (300 mL), and lithium methanolate (6.07 mL, 6.07 mmol, 1 M) was added. The reaction mixture was heated to 100° C. To this mixture was added 1,1-dimethoxy-N,N-dimethylmethanamine (64.5 mL, 486 mmol) over 10 minutes. The reaction mixture was stirred at 95° C. for 16 hours. The reaction mixture was cooled to room temperature and water was added carefully (300 mL, exothermic). The resulting precipitate was collected by vacuum filtration, washed with water, and dried to provide (E)-2-(5-bromo-2-methoxy-3-nitropyridin-4-yl)-N,N-dimethylethenamine (13.9 g, 45.9 mmol, 76% yield).

Step 4A (E)-2-(5-bromo-2-methoxy-3-nitropyridin-4-yl)-N,N-dimethylethenamine (13.9 g, 45.8 mmol) and ethyl acetate (150 mL) were added to Ra-Ni 2800 (pre-washed with ethanol), water slurry (6.9 g, 118 mmol) in a stainless steel pressure bottle and stirred for 30 minutes at 30 psi of hydrogen and room temperature. The reaction mixture was filtered, and concentrated. The residue was triturated with dichloromethane, and the solid collected by filtration to provide 4-bromo-7-methoxy-1H-pyrrolo[2,3-c]pyridine (5.82 g). The mother liquor was evaporated and the residue triturated again with dichloromethane and filtered to provide an additional 1.63 g of 4-bromo-7-methoxy-1H-pyrrolo[2,3-c]pyridine. Total yield=7.45 g, 72% yield.

Step 5A

A solution of 4-bromo-7-methoxy-1H-pyrrolo[2,3-c]pyridine (7.42 g, 32.7 mmol) in dimethylformamide (235 mL) was stirred at room temperature. To this solution was added sodium hydride (1.18 g, 1.96 g of 60% dispersion in oil, 49.0 mmol), and the reaction mixture was stirred for 10 minutes. P-toluenesulfonyl chloride (9.35 g, 49.0 mmol) was then added portion-wise, and the mixture was stirred at room temperature under nitrogen for 16 hours. The reaction mixture was quenched carefully with water and the resulting beige solid collected by vacuum filtration on a Buchner funnel, and washed with water. The solid was collected and dried in a vacuum oven at 50° C. to provide 12.4 g (100%) of 4-bromo-7-methoxy-1-tosyl-1H-pyrrolo[2,3-c]pyridine.

Step 6A

A solution of 4-bromo-7-methoxy-1-tosyl-1H-pyrrolo[2,3-c]pyridine (12.4 g, 32.6 mmol) in dioxane (140 mL) was stirred at room temperature. To this solution was added 4M HCl in dioxane (140 mL). The reaction mixture was stirred at 40° C. for 16 hours. The reaction mixture was cooled to room temperature and concentrated. The residue was triturated with diethyl ether, filtered, and rinsed with additional diethyl ether and dried to provide 4-bromo-1-tosyl-1H-pyrrolo[2,3-c]pyridin-7(6H)-one (11.23 g, 30.6 mmol, 94% yield) as a beige solid.

Step 7A

Sodium hydride (0.875 g, 36.5 mmol, 1.46 g of a 60% in oil dispersion) was added to a stirring solution of 4-bromo-1-tosyl-1H-pyrrolo[2,3-c]pyridin-7(6H)-one (11.2 g, 30.4 mmol) in dimethylformamide (217 mL) under nitrogen. After 30 minutes, iodomethane (2.27 mL, 36.5 mmol) was added and the solution was stirred at room temperature for 3 h. Upon addition of water (250 mL) a precipitate formed. The precipitate was collected by vacuum filtration, rinsed with water (50 mL) and dried in a vacuum oven at 55° C. overnight to provide 11.2 g of 4-bromo-6-methyl-1-tosyl-1H-pyrrolo[2,3-c]pyridin-7(6H)-one (96%).

Step 8A

4-Bromo-6-methyl-1-tosyl-1H-pyrrolo[2,3-c]pyridin-7(6H)-one (6.55 g, 17.2 mmol), 4,4,4',4',5,5,5',5'-octamethyl-2,2'-bi(1,3,2-dioxaborolane) (8.73 g, 34.4 mmol), potassium acetate (3.71 g, 37.8 mmol), tris(dibenzylideneacetone)dipalladium(0) (0.393 g, 0.430 mmol) and 2-dicyclohexylphosphino-2',4',6'-triisopropylbiphenyl (X-PHOS, 0.819 g, 1.72 mmol) were combined and sparged with argon for 1 hour with stirring. Dioxane (86 mL) was sparged with nitrogen for 1 hour, transferred via cannula under nitrogen to the solid components, and the mixture was heated under argon at 80° C. for 5 hours. The reaction mixture was cooled to room temperature, partitioned between ethyl acetate and water, and filtered through Celite. The ethyl acetate layer was washed twice with brine, dried (Na$_2$SO$_4$), filtered and concentrated. The residue was purified by chromatography (silica gel, 25-80% ethyl acetate in hexane). The resulting material from chromatography was triturated with a minimal amount of hexanes (30 mL) and the particulate solid was collected by filtration, rinsed with a minimal amount of hexanes and dried to constant mass to afford 6-methyl-4-(4,4,5,5-tetramethyl-1,3,2-dioxaborolan-2-yl)-1-tosyl-1H-pyrrolo[2,3-c]pyridin-7(6H)-one (5.4 g, 73%).

Step 9A

A mixture of 3-bromo-4-(2,4-difluorophenoxy)aniline (5.0 g, 11.67 mmol), 6-methyl-4-(4,4,5,5-tetramethyl-1,3,2-dioxaborolan-2-yl)-1-tosyl-1H-pyrrolo[2,3-c]pyridin-7(6H)-one (3.85 g, 12.84 mmol), 1,3,5,7-tetramethyl-6-phenyl-2,4,8-trioxa-6-phosphaadamantane (0.399 g, 1.366 mmol), tris(dibenzylideneacetone)dipalladium(0) (0.321 g, 0.350 mmol), and potassium phosphate (6.19 g, 29.2 mmol) in dioxane (50 mL) and water (12.5 mL) was degassed and back-filled with nitrogen several times. The reaction mixture was heated at 60° C. for 16 hours and then cooled to ambient temperature. The reaction mixture was partitioned between water and ethyl acetate. The aqueous layer was extracted with additional ethyl acetate three times. The combined organic layers were washed with brine, dried over anhydrous magnesium sulfate, filtered, and concentrated. The residue was purified by flash column chromatography (silica gel, 60% ethyl acetate/hexanes) to provide 4-(5-amino-2-(2,4-difluorophenoxy)phenyl)-6-methyl-1-tosyl-1H-pyrrolo[2,3-c]pyridin-7(6H)-one (4.40 g, 72.3% yield).

Step 10A

A solution of 4-(5-amino-2-(2,4-difluorophenoxy)phenyl)-6-methyl-1-tosyl-1H-pyrrolo[2,3-c]pyridin-7(6H)-one (4.35 g, 8.34 mmol) in dichloromethane (50 mL) was cooled to 0° C. To this solution was added ethanesulfonyl chloride (2.37 mL, 25.0 mmol). The reaction mixture was stirred at room temperature for 2 hours. The solvent was evaporated, and the residue was partitioned between ethyl acetate and water. The aqueous layer was extracted with additional ethyl acetate twice. The combined organic layers were washed with saturated aqueous sodium chloride, dried over anhydrous magnesium sulfate, filtered, and concentrated. The residue was purified by flash chromatography (silica gel, 80% ethyl acetate/hexanes) to provide N-(4-(2,4-difluorophenoxy)-3-(6-methyl-7-oxo-1-tosyl-6,7-dihydro-1H-pyrrolo[2,3-c]pyridin-4-yl)phenyl)-N-(ethylsulfonyl)ethanesulfonamide (5.34 g, 91% yield).

Step 11A

A mixture of N-(4-(2,4-difluorophenoxy)-3-(6-methyl-7-oxo-1-tosyl-6,7-dihydro-1H-pyrrolo[2,3-c]pyridin-4-yl)phenyl)-N-(ethylsulfonyl)ethanesulfonamide (5.3 g, 7.5 mmol), potassium hydroxide (8.43 g, 150 mmol), and N,N,N-trimethylhexadecan-1-aminium bromide (0.137 g, 0.375 mmol) in tetrahydrofuran (60 mL) and water (30 mL) was heated at 90° C. for 16 hours. Tetrahydrofuran was removed under reduced pressure, and the residue was partitioned between water and ethyl acetate. The aqueous layer was neutralized to pH=7 using 10% HCl. The aqueous layer was then extracted with ethyl acetate. The combined organic layers were washed with saturated aqueous sodium chloride, dried over anhydrous magnesium sulfate, filtered, and concentrated. The residue was purified by flash chromatography (silica gel, ethyl acetate). The desired fractions were combined and concentrated. The residue was triturated with 20 mL of acetonitrile to provide N-[4-(2,4-difluorophenoxy)-3-(6-methyl-7-oxo-6,7-dihydro-1H-pyrrolo[2,3-c]pyridin-4-yl)phenyl]ethanesulfonamide Form I (2.82 g, 82% yield). $^1$H NMR (300 MHz, DMSO-d$_6$) δ 1.23 (t, J=7.3 Hz, 3H), 3.11 (q, J=7.3 Hz, 2H), 3.53 (s, 3H), 6.27-6.22 (m, 1H), 6.91 (d, J=8.7 Hz, 1H), 7.13-6.93 (m, 2H), 7.19 (dd, J=8.8, 2.7 Hz, 1H), 7.32-7.25 (m, 2H), 7.42-7.31 (m, 2H), 9.77 (s, 1H), 12.04 (bs, 1H). MS (ESI+) m/z 460.1 (M+H)$^+$.

Figure 2:
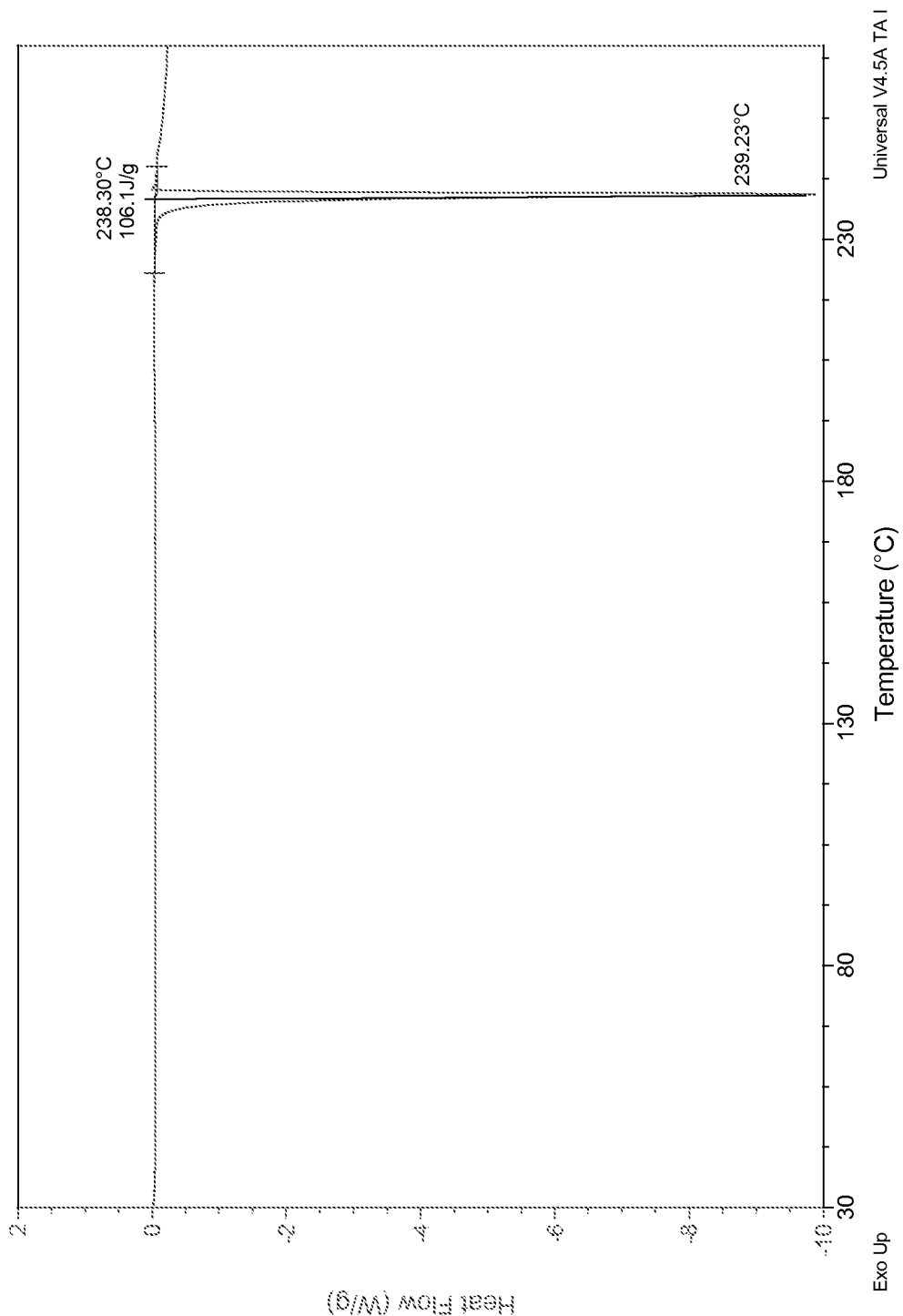
FIG. 2 provides a differential scanning calorimeter (DSC) thermogram of N-[4-(2,4-difluorophenoxy)-3-(6-methyl-7-oxo-6,7-dihydro-1H-pyrrolo[2,3-c]pyridin-4-yl)phenyl]ethanesulfonamide Form I.
Figure 3:
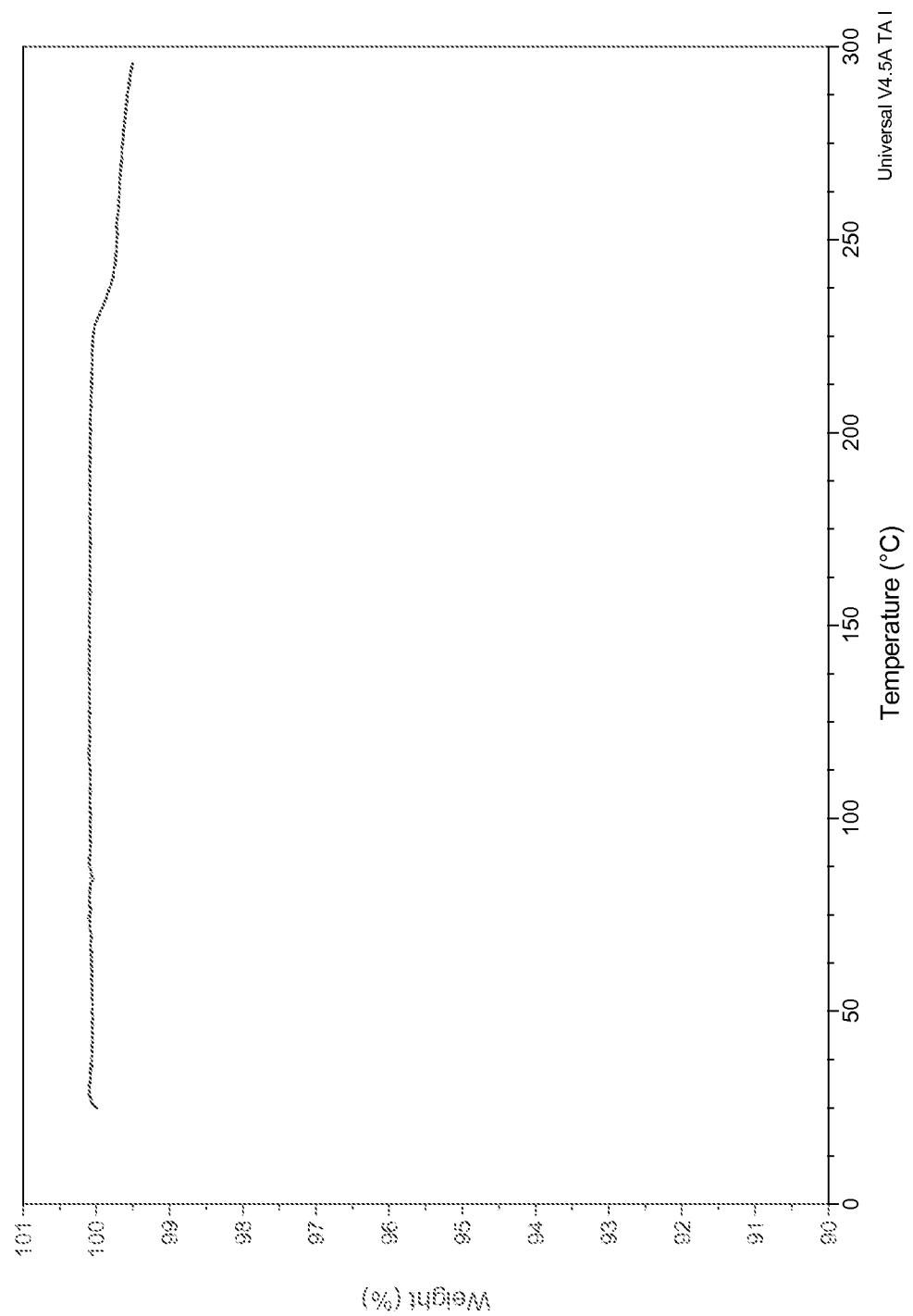
FIG. 3 provides a TGA curve of N-[4-(2,4-difluorophenoxy)-3-(6-methyl-7-oxo-6,7-dihydro-1H-pyrrolo[2,3-c]pyridin-4-yl)phenyl]ethanesulfonamide Form I.

PXRD analysis of the Form I solid provided the X-ray diffraction peaks listed in Table 1. A portion of Form I solid was removed, heated to 190° C., and then cooled to room temperature. The resulting material when analyzed by PXRD provided the X-ray diffraction peaks listed in Table 2. The DSC thermogram for this material is depicted in FIG. 2. The melting of Form I occurred at about 238.30° C. The TGA curve for this material is depicted in FIG. 3.

Figure 5:
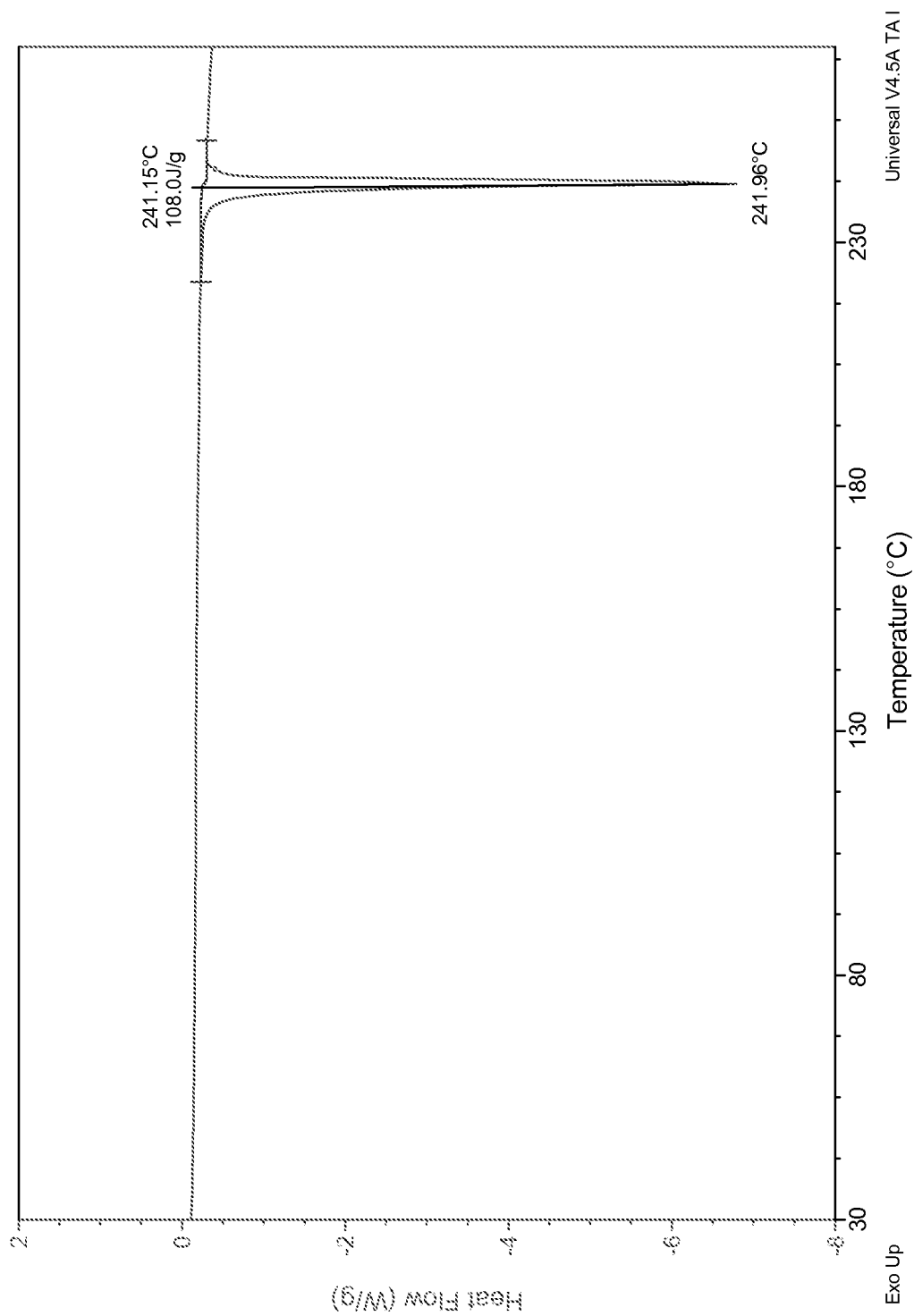
FIG. 5 provides a differential scanning calorimeter (DSC) thermogram of N-[4-(2,4-difluorophenoxy)-3-(6-methyl-7-oxo-6,7-dihydro-1H-pyrrolo[2,3-c]pyridin-4-yl)phenyl]ethanesulfonamide Form II.
Figure 6:
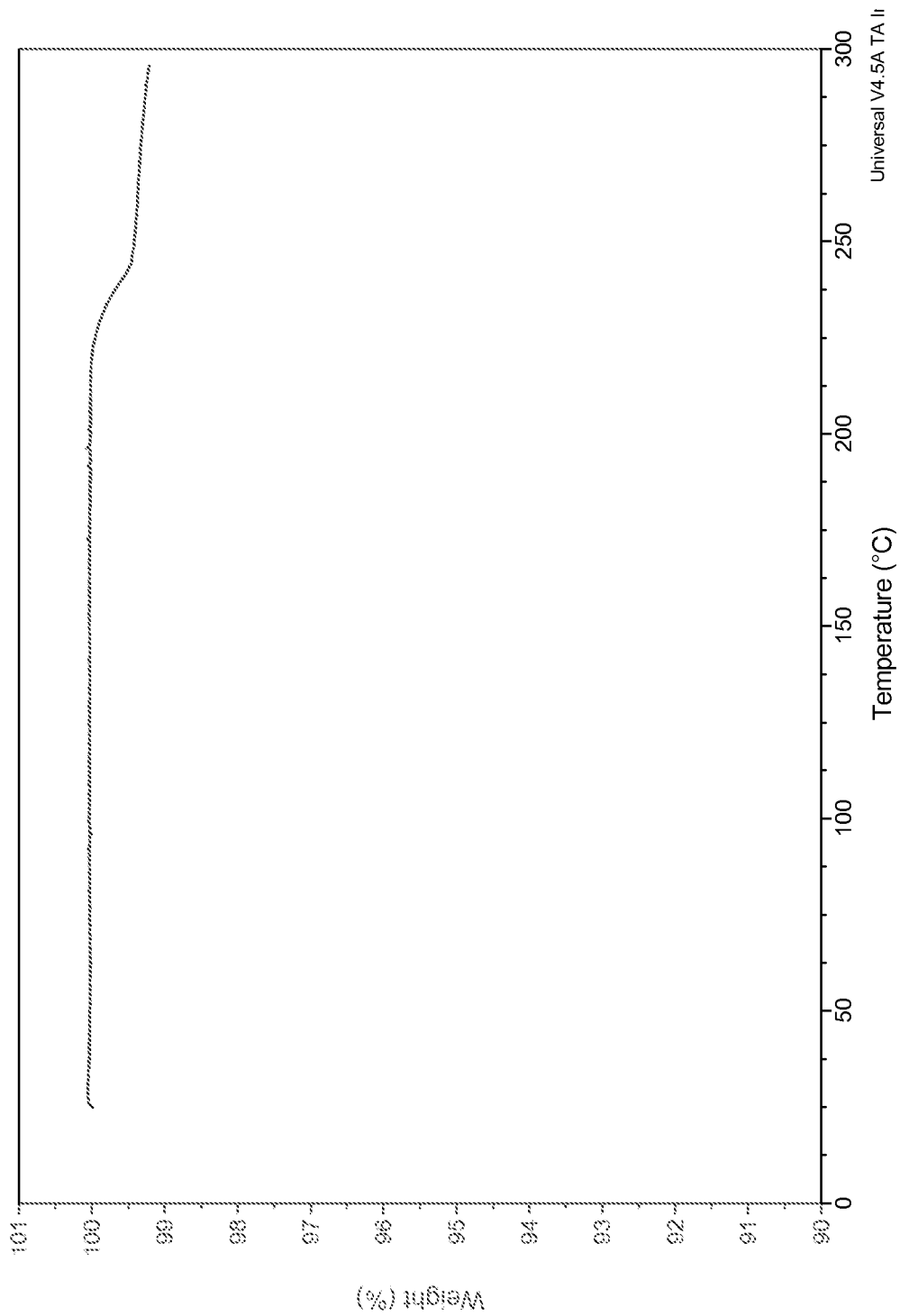
FIG. 6 provides a TGA curve of N-[4-(2,4-difluorophenoxy)-3-(6-methyl-7-oxo-6,7-dihydro-1H-pyrrolo[2,3-c]pyridin-4-yl)phenyl]ethanesulfonamide Form II.

Representative thermal characteristics of Form II are shown in FIGS. 5 and 6. The melting of Form II occurred at about 241.15° C.

TABLE 1

Peak Listing of N-[4-(2,4-difluorophenoxy)-3-(6-methyl-7-oxo-6,7-dihydro-1H-pyrrolo[2,3-c]pyridin-4-yl)phenyl]ethanesulfonamide Form I

| Peak Position (° 2θ) | Relative Intensity |
| --- | --- |
| 8.5 | 100.0 |
| 10.8 | 23.0 |
| 11.1 | 7.9 |
| 11.3 | 12.5 |
| 11.7 | 12.0 |
| 12.9 | 7.4 |
| 13.8 | 3.7 |
| 14.4 | 18.7 |
| 15.0 | 2.0 |
| 16.2 | 3.0 |
| 16.5 | 3.6 |
| 17.1 | 11.4 |
| 17.3 | 15.0 |
| 17.4 | 6.2 |
| 17.8 | 4.3 |
| 18.5 | 13.9 |
| 18.8 | 14.1 |
| 19.3 | 9.0 |
| 19.5 | 26.8 |
| 20.2 | 8.7 |
| 20.6 | 30.2 |
| 21.5 | 18.8 |
| 22.6 | 19.5 |
| 23.2 | 9.8 |
| 23.5 | 20.7 |
| 23.9 | 3.4 |
| 24.4 | 12.3 |
| 25.1 | 15.2 |

TABLE 2

Peak Listing of N-[4-(2,4-difluorophenoxy)-3-(6-methyl-7-oxo-6,7-dihydro-1H-pyrrolo[2,3-c]pyridin-4-yl)phenyl]ethanesulfonamide Form I

| Peak Position (° 2θ) | Relative Intensity |
| --- | --- |
| 8.5 | 100.0 |
| 10.8 | 22.0 |
| 11.1 | 8.5 |
| 11.3 | 14.9 |
| 11.7 | 13.2 |
| 13.0 | 6.2 |
| 13.8 | 3.2 |
| 14.5 | 21.7 |
| 15.1 | 3.1 |
| 16.2 | 2.8 |
| 16.6 | 3.3 |
| 17.1 | 12.3 |
| 17.4 | 18.4 |
| 17.5 | 7.6 |
| 17.9 | 4.6 |
| 18.5 | 14.9 |
| 18.9 | 16.1 |
| 19.4 | 10.0 |
| 19.6 | 33.9 |
| 20.3 | 8.5 |
| 20.7 | 35.6 |
| 21.6 | 20.5 |
| 22.7 | 21.7 |
| 23.3 | 10.6 |
| 23.6 | 21.5 |
| 23.9 | 3.8 |
| 24.5 | 10.1 |
| 25.2 | 18.7 |

Preparation of N-[4-(2,4-difluorophenoxy)-3-(6-methyl-7-oxo-6,7-dihydro-1H-pyrrolo[2,3-c]pyridin-4-yl)phenyl]ethanesulfonamide Form II Step 1B 3-Bromo-4-(2,4-difluorophenoxy)aniline (3.24 g, 10.80 mmol) and triethylamine (4.37 g, 43.2 mmol) were stirred in dichloromethane (48.1 mL) at ambient temperature. Ethanesulfonyl chloride (4.16 g, 32.4 mmol) was added dropwise and the solution stirred at ambient temperature for 1 hour. The reaction mixture was concentrated under reduced pressure, dioxane (24 mL) and sodium hydroxide (10% w/v, 12 mL, 0.427 mmol) were added, and the solution was heated to 70° C. for 1 hour. The solution was neutralized to a pH of about 7 with saturated aqueous NH$_4$Cl (200 mL). The aqueous phase was extracted with ethyl acetate (3×125 mL). The combined organics were washed with brine, dried (anhydrous MgSO$_4$), filtered, and then concentrated under reduced pressure. The residue was purified by flash chromatography (silica gel, 0-50% ethyl acetate/petroleum ether gradient,) to afford N-(3-bromo-4-(2,4-difluorophenoxy)phenyl)ethanesulfonamide (1.4 g, 3.57 mmol, 33.1% yield).

Step 2B

A mixture of 6-methyl-4-(4,4,5,5-tetramethyl-1,3,2-dioxaborolan-2-yl)-1-tosyl-1H-pyrrolo[2,3-c]pyridin-7(6H)-one (6.00 g, 14.0 mmol), N-(3-bromo-4-(2,4-difluorophenoxy)phenyl)ethanesulfonamide (5.77 g, 14.7 mmol), 1,3,5,7-tetramethyl-6-phenyl-2,4,8-trioxa-6-phosphaadamantane (0.205 g, 0.700 mmol), tris(dibenzylideneacetone)dipalladium(0) (0.321 g, 0.350 mmol) and potassium phosphate (2.97 g, 14.0 mmol) was combined and sparged with argon for 30 minutes. A mixture of dioxane (60 mL) and water (15 mL) was sparged with nitrogen for 30 minutes and transferred by syringe into the reaction vessel under argon. The reaction mixture was stirred at 60° C. for 2 hours, cooled to ambient temperature, and partitioned between ethyl acetate and water. The organic layer was washed with brine, dried (anhydrous sodium sulfate), treated with silica gel (2-4 g) for 45 minutes, filtered and concentrated to afford N-(4-(2,4-difluorophenoxy)-3-(6-methyl-7-oxo-1-tosyl-6,7-dihydro-1H-pyrrolo[2,3-c]pyridin-4-yl)phenyl)ethanesulfonamide (8 g, 13.04 mmol, 93% yield).

Step 3B

N-(4-(2,4-difluorophenoxy)-3-(6-methyl-7-oxo-1-tosyl-6,7-dihydro-1H-pyrrolo[2,3-c]pyridin-4-yl)phenyl)ethanesulfonamide (8.0 g, 13 mmol), N,N,N-trimethylhexadecan-1-aminium bromide (0.238 g, 0.652 mmol) and potassium hydroxide (11.9 g, 211 mmol) were combined in tetrahydrofuran (66 mL) and water (22 mL) and the mixture heated at 100° C. for 14 hours. The reaction mixture was cooled to ambient temperature and partitioned between ethyl acetate and water and the pH was adjusted to about 7 by careful addition of concentrated HCl. The organic layer was separated, washed three times with saturated aqueous sodium chloride, dried (anhydrous Na$_2$SO$_4$), filtered, and concentrated. The residue was suspended in dichloromethane and heated under reflux for four hours and then cooled to room temperature. The resulting solid was isolated by filtration and rinsed with dichloromethane and hexanes to afford a mixture of N-(4-(2,4-difluorophenoxy)-3-(6-methyl-7-oxo-6,7-dihydro-1H-pyrrolo[2,3-c]pyridin-4-yl)phenyl)ethanesulfonamide Form I and Form II (4.2 g, 9.14 mmol, 70.1% yield).

Step 4B

A portion of the mixture of Form I and Form II from Step 3B (7.5 g, 16.32 mmol), was dissolved in a solvent mixture of boiling ethyl acetate (1500 mL) and ethanol (50 mL). Heating was discontinued and the hot solution was treated with 3-mercaptopropyl functionalized silica gel (Aldrich, catalog number 538086, 10 g) and Darco G-60 (10 g), stirred for 20 minutes, filtered through a 0.5 inch deep pad of Celite and the filtrate was concentrated. The resulting solid was stirred in refluxing ethanol (150 mL) for two hours, cooled to ambient temperature and the solid was collected by filtration and dried to constant mass (6.517 g, 87% recovery) to provide N-(4-(2, 4-difluorophenoxy)-3-(6-methyl-7-oxo-6,7-dihydro-1H-pyrrolo[2,3-c]pyridin-4-yl)phenyl)ethanesulfonamide Form II.

Form II solid gives X-ray diffraction peaks listed in Table 3. A portion of Form II solid generated in Step 4B above was removed, heated to 190° C., and then cooled to room temperature. The resulting solid when analyzed by PXRD provided the X-ray diffraction peaks listed in Table 4. The DSC thermogram for this material is depicted in FIG. 5. The melting of Form II occurred at about 241.15° C. The TGA curve for this material is depicted in FIG. 6.

TABLE 3

Peak Listing N-[4-(2,4-difluorophenoxy)-3-(6-methyl-7-oxo-6,7-dihydro-1H-pyrrolo[2,3-c]pyridin-4-yl)phenyl]ethanesulfonamide Form II

| Peak Position (° 2θ) | Relative Intensity |
| --- | --- |
| 6.2 | 11.7 |
| 9.0 | 6.7 |
| 11.0 | 5.4 |
| 12.2 | 18.4 |
| 12.6 | 16.2 |
| 13.1 | 48.1 |
| 14.1 | 12.1 |
| 15.5 | 5.8 |
| 16.3 | 13.0 |
| 16.5 | 16.9 |
| 16.9 | 23.2 |
| 17.8 | 32.7 |
| 18.0 | 100.0 |
| 18.3 | 15.3 |
| 18.9 | 60.1 |
| 20.4 | 8.7 |
| 21.0 | 13.5 |
| 21.6 | 13.5 |
| 21.8 | 29.7 |
| 22.1 | 24.3 |
| 22.9 | 8.9 |
| 23.2 | 6.2 |
| 24.4 | 11.0 |
| 24.6 | 16.0 |
| 25.5 | 19.6 |
| 26.3 | 30.1 |
| 26.9 | 20.2 |
| 27.2 | 12.1 |

TABLE 4

Peak Listing N-[4-(2,4-difluorophenoxy)-3-(6-methyl-7-oxo-6,7-dihydro-1H-pyrrolo[2,3-c]pyridin-4-yl)phenyl]ethanesulfonamide Form II

| Peak Position (° 2θ) | Relative Intensity |
| --- | --- |
| 6.2 | 10.1 |
| 9.0 | 6.9 |
| 11.0 | 5.1 |
| 12.3 | 20.3 |
| 12.6 | 19.7 |
| 13.1 | 50.5 |
| 14.1 | 13.5 |
| 15.6 | 5.1 |
| 16.4 | 17.5 |
| 16.5 | 20.3 |
| 16.9 | 24.1 |
| 17.8 | 33.2 |
| 18.1 | 100.0 |
| 18.3 | 14.2 |
| 18.9 | 70.0 |
| 20.4 | 8.3 |
| 21.1 | 15.8 |
| 21.6 | 14.9 |
| 21.8 | 36.2 |
| 22.1 | 25.5 |
| 22.9 | 10.3 |
| 23.2 | 6.1 |
| 24.4 | 13.2 |
| 24.7 | 17.0 |
| 25.6 | 26.4 |
| 26.3 | 41.9 |
| 27.0 | 21.9 |
| 27.3 | 12.4 |

The invention claimed is:

1. An isolated crystalline form of N-[4-(2,4-difluorophenoxy)-3-(6-methyl-7-oxo-6,7-dihydro-1H-pyrrolo[2,3-c]pyridin-4-yl)phenyl]ethanesulfonamide, wherein the crystalline form has a powder X-ray diffraction pattern comprising three or more 2θ peak values ±0.2 selected from the group consisting of: 6.2°, 9.0°, 12.3°, 12.6°, 15.6°, 22.1°, 25.6°, 26.3°, 27.0°, and 27.3°.

2. An isolated crystalline form of N-[4-(2,4-difluorophenoxy)-3-(6-methyl-7-oxo-6,7-dihydro-1H-pyrrolo[2,3-c]pyridin-4-yl)phenyl]ethanesulfonamide, wherein the crystalline form has a powder X-ray diffraction pattern comprising the following 2θ peak values ±0.2: 6.2°, 9.0°, 11.0°, 12.3°, 12.6°, 13.1°, 14.1°, 15.6°, 16.4°, 16.5°, 16.9°, 17.8°, 18.1°, 18.3°, 18.9°, 20.4°, 21.1°, 21.6°, 21.8°, 22.1°, 22.9°, 23.2°, 24.4°, 24.7°, 25.6°, 26.3°, 27.0°, and 27.3°.

3. The crystalline form of claim 1 having a powder X-ray diffraction pattern comprising three, four, five, or six 2θ peak values ±0.2 selected from the group consisting of 6.2°, 9.0°, 12.3°, 12.6, 15.6°, 22.1°, 25.6°, 26.3°, 27.0°, and 27.3°.

4. The crystalline form of claim 1 having a powder X-ray diffraction pattern comprising six 2θ peak values ±0.2 selected from the group consisting of 6.2°, 9.0°, 12.3°, 12.6, 15.6°, 22.1°, 25.6°, 26.3°, 27.0°, and 27.3°.

5. The crystalline form of claim 1 having a powder X-ray diffraction pattern comprising five 2θ peak values ±0.2 selected from the group consisting of 6.2°, 9.0°, 12.3°, 12.6, 15.6°, 22.1°, 25.6°, 26.3°, 27.0°, and 27.3°.

6. The crystalline form of claim 1 having a powder X-ray diffraction pattern comprising four 2θ peak values ±0.2 selected from the group consisting of 6.2°, 9.0°, 12.3°, 12.6, 15.6°, 22.1°, 25.6°, 26.3°, 27.0°, and 27.3°.

7. The crystalline form of claim 1 having a powder X-ray diffraction pattern comprising three 2θ peak values ±0.2 selected from the group consisting of 6.2°, 9.0°, 12.3°, 12.6, 15.6°, 22.1°, 25.6°, 26.3°, 27.0°, and 27.3°.

8. The crystalline form of claim 1 having a powder X-ray diffraction pattern comprising the following 2θ peak values ±0.2: 6.2°, 9.0°, 12.3°, 12.6°, and 15.6°.

9. The crystalline form of claim 1 having a powder X-ray diffraction pattern comprising the following 2θ peak values ±0.2: 22.1°, 25.6°, 26.3°, 27.0°, and 27.3°.

10. The crystalline form of claim 2 having a powder X-ray diffraction pattern comprising peak values ±0.2 at 2θ positions 6.2°, 9.0°, 12.3°, 12.6°, 13.1°, 14.1°, 16.4°, 16.5°, 16.9°, 17.8°, 18.1°, 18.3°, and 18.9°.

11. The crystalline form of claim 2 having a powder X-ray diffraction pattern comprising peak values ±0.2 at 2θ positions 6.2°, 9.0°, 12.3°, 12.6°, 13.1°, 14.1°, 18.1°, and 18.9°.

12. The crystalline form of claim 2 having a powder X-ray diffraction pattern comprising peak values ±0.2 at 2θ positions 6.2°, 9.0°, 12.3°, 12.6°, 13.1°, and 18.1°.

13. The crystalline form of claim 2 having a powder X-ray diffraction pattern comprising peak values ±0.2 at 2θ positions 9.0°, 12.3°, 12.6°, 13.1°, and 18.1°.

14. The crystalline form of claim 1 having a differential scanning calorimetry thermogram endotherm between 240 and 242° C.

15. The crystalline form of claim 1 having a differential scanning calorimetry thermogram endotherm at approximately 241° C.

16. A pharmaceutical composition comprising an isolated crystalline form of N-[4-(2,4-difluorophenoxy)-3-(6-methyl-7-oxo-6,7-dihydro-1H-pyrrolo[2,3-c]pyridin-4-yl)phenyl]ethanesulfonamide according to claim 1, and at least one pharmaceutically acceptable carrier.

17. A method for treating cancer in a subject comprising administering a therapeutically effective amount of a pharmaceutical composition comprising a crystalline form of N-[4-(2,4-difluorophenoxy)-3-(6-methyl-7-oxo-6,7-dihydro-1H-pyrrolo[2,3-c]pyridin-4-yl)phenyl]ethanesulfonamide according to claim 1 and at least one pharmaceutically acceptable carrier, to a subject in need thereof.

18. The method of claim 17 wherein the cancer is selected from the group consisting of: acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenström's macroglobulinemia, testicular tumors, uterine cancer and Wilms' tumor.

19. A method of making a pharmaceutical composition comprising N-[4-(2,4-difluorophenoxy)-3-(6-methyl-7-oxo-6,7-dihydro-1H-pyrrolo[2,3-c]pyridin-4-yl)phenyl]ethanesulfonamide and a pharmaceutically acceptable carrier, comprising:
mixing an isolated crystalline form of N-[4-(2,4-difluorophenoxy)-3-(6-methyl-7-oxo-6,7-dihydro-1H-pyrrolo[2,3-c]pyridin-4-yl)phenyl]ethanesulfonamide, wherein the crystalline form has a powder X-ray diffraction pattern comprising three or more 2θ peak values ±0.2 selected from the group consisting of: 6.2°, 9.0°, 12.3°, 12.6°, 15.6°, 22.1°, 25.6°, 26.3°, 27.0°, and 27.3°, with a pharmaceutically acceptable carrier.

20. A composition comprising greater than 90% (w/w) crystalline form II of N-[4-(2,4-difluorophenoxy)-3-(6-methyl-7-oxo-6,7-dihydro-1H-pyrrolo[2,3-c]pyridin-4-yl)phenyl]ethanesulfonamide, wherein the crystalline form has a powder X-ray diffraction pattern comprising three or more 2θ peak values ±0.2 selected from the group consisting of: 6.2°, 9.0°, 12.3°, 12.6°, 15.6°, 22.1°, 25.6°, 26.3°, 27.0°, and 27.3°.

21. A method for treating an acute kidney disease or condition in a subject comprising administering a therapeutically effective amount of a pharmaceutical composition comprising a crystalline form of N-[4-(2,4-difluorophenoxy)-3-(6-methyl-7-oxo-6,7-dihydro-1H-pyrrolo[2,3-c]pyridin-4-yl)phenyl]ethanesulfonamide according to claim 1 and at least one pharmaceutically acceptable carrier, to a subject in need thereof, wherein said acute kidney disease or condition is selected from the group consisting of: ischemia-reperfusion induced kidney disease, cardiac and major surgery induced kidney disease, percutaneous coronary intervention induced kidney disease, radio-contrast agent induced kidney disease, sepsis induced kidney disease, pneumonia induced kidney disease, and drug toxicity induced kidney disease.

22. A method for treating a chronic kidney disease or condition in a subject comprising administering a therapeutically effective amount of a pharmaceutical composition comprising a crystalline form of N-[4-(2,4-difluorophenoxy)-3-(6-methyl-7-oxo-6,7-dihydro-1H-pyrrolo[2,3-c]pyridin-4-yl)phenyl]ethanesulfonamide according to claim 1 and at least one pharmaceutically acceptable carrier, to a subject in need thereof, wherein said chronic kidney disease or condition is selected from the group consisting of: diabetic nephropathy, hypertensive nephropathy, HIV-associated nephropathy, glomerulonephritis, lupus nephritis, IgA nephropathy, focal segmental glomerulosclerosis, membranous glomerulonephritis, minimal change disease, polycystic kidney disease and tubular interstitial nephritis.

23. A method for treating a disease or condition in a subject comprising administering a therapeutically effective amount of a pharmaceutical composition comprising a crystalline form of N-[4-(2,4-difluorophenoxy)-3-(6-methyl-7-oxo-6,7-dihydro-1H-pyrrolo[2,3-c]pyridin-4-yl)phenyl]ethanesulfonamide according to claim 1 and at least one pharmaceutically acceptable carrier, to a subject in need thereof, wherein said disease or condition is selected from the group consisting of Addison's disease, acute gout, ankylosing spondylitis, asthma, atherosclerosis, Behcet's disease, bullous skin diseases, cardiac myopathy, cardiac hypertrophy, chronic obstructive pulmonary disease (COPD), Crohn's disease, dermatitis, eczema, giant cell arteritis, glomerulonephritis, heart failure, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis.

24. A method for treating an acquired immunodeficiency syndrome (AIDS) in a subject comprising administering a therapeutically effective amount of a pharmaceutical composition comprising a crystalline form of N-[4-(2,4-difluorophenoxy)-3-(6-methyl-7-oxo-6,7-dihydro-1H-pyrrolo[2,3-c]pyridin-4-yl)phenyl]ethanesulfonamide according to claim 1 and at least one pharmaceutically acceptable carrier, to a subject in need thereof.

25. A method for treating a disease or condition in a subject comprising administering a therapeutically effective amount of a pharmaceutical composition comprising a crystalline form of N-[4-(2,4-difluorophenoxy)-3-(6-methyl-7-oxo-6,7-dihydro-1H-pyrrolo[2,3-c]pyridin-4-yl)phenyl]ethanesulfonamide according to claim 1 and at least one pharmaceutically acceptable carrier, to a subject in need thereof, wherein said disease or condition is selected from the group consisting of: obesity, dyslipidemia, hypercholesterolemia, Alzheimer's disease, metabolic syndrome, hepatic steatosis, type II diabetes, insulin resistance, diabetic retinopathy and diabetic neuropathy.

26. A method of contraception in a male subject comprising administering a therapeutically effective amount of a pharmaceutical composition comprising a crystalline form of N-[4-(2,4-difluorophenoxy)-3-(6-methyl-7-oxo-6,7-dihydro-1H-pyrrolo[2,3-c]pyridin-4-yl)phenyl]ethanesulfonamide according to claim 1 and at least one pharmaceutically acceptable carrier, to a subject in need thereof.

* * * * *